United States Patent [19]
Wang et al.

[11] Patent Number: 5,348,853
[45] Date of Patent: Sep. 20, 1994

[54] METHOD FOR REDUCING NON-SPECIFIC PRIMING IN DNA AMPLIFICATION

[75] Inventors: Chang-Ning J. Wang, Chelmsford; Kai-Wuan Wu, Lowell, both of Mass.

[73] Assignee: Biotronics Corporation, Lowell, Mass.

[21] Appl. No.: 808,463

[22] Filed: Dec. 16, 1991

[51] Int. Cl.$^5$ .......................... C12Q 1/68; C12P 19/34
[52] U.S. Cl. .......................................... 435/6; 435/91.2
[58] Field of Search .............................. 435/6, 91, 91.2

[56] References Cited

U.S. PATENT DOCUMENTS

| | | | |
|---|---|---|---|
| 4,683,194 | 7/1987 | Saiki et al. | 435/6 |
| 4,683,195 | 7/1987 | Mullis et al. | 435/6 |
| 4,683,202 | 7/1987 | Mullis | 435/91 |
| 4,725,537 | 2/1988 | Fritsch et al. | 435/6 |
| 4,800,159 | 1/1989 | Mullis et al. | 435/172.3 |
| 4,822,733 | 4/1989 | Morrison | 435/6 |
| 4,965,188 | 10/1990 | Mullis et al. | 435/6 |
| 4,996,143 | 2/1991 | Heller et al. | 435/6 |
| 5,038,852 | 8/1991 | Johnson et al. | 165/12 |

FOREIGN PATENT DOCUMENTS

| | | | |
|---|---|---|---|
| 0200362A2 | 12/1986 | European Pat. Off. | C12Q 1/68 |
| 0201184A2 | 12/1986 | European Pat. Off. | C12P 19/34 |
| 0236069 | 9/1987 | European Pat. Off. | G05D 23/19 |
| 0320308 | 6/1989 | European Pat. Off. | C12Q 1/68 |
| 0333465 | 9/1989 | European Pat. Off. | C12Q 1/68 |
| 0382433A2 | 8/1990 | European Pat. Off. | C12Q 1/68 |
| WO89/09835 | 10/1989 | PCT Int'l Appl. | C12Q 1/68 |

OTHER PUBLICATIONS

Blanco, L. et al. Highly efficient DNA synthesis by the phage 029DNA polymerase (J. Biol. Chem. (1989) 264:8935–8940.

Morrison, L. E., Halder, T. C. and Stols, L. M., "Solution-Phase Detection of Polynucleotides Using Interacting Fluorescent Labels and Competitive Hybridization", Analytical Biochemistry 183:231-244 (1989).

P. Holland et al., "Detection of specific polymerase chain reaction product . . . ", Proc. Natl. Acad. Sci. USA 88:7276-7280 (1991).

G. T. Walker et al., "Isothermal in vitro amplification of DNA by a restriction enzyme/DNA polymerase system", P.N.A.S. 89:392-396 (1992).

Primary Examiner—Margaret Parr
Assistant Examiner—David Schreiber
Attorney, Agent, or Firm—Wolf, Greenfield & Sacks

[57] ABSTRACT

This invention relates to a homogeneous process for amplifying a target sequence in a nucleic acid sample and detecting amplification in the absence of a separation step. The invention further provides a method for nucleic acid amplification under conditions which substantially reduce the occurrence of nonspecific amplification. Products and an apparatus related to the homogeneous process are also described.

16 Claims, 22 Drawing Sheets

Template:

3'-TGGGCCCCTAGGAGATATCTCAGCTGGAC-5'

(Sequence I.D. Number 3)

Extension Probe: 5'-ACCCGGGGATCCTCTA-3'

(Sequence I.D. Number 1)

Lagging Probe:

5'-AGAGTCGACCTGCA-3'

(Sequence I.D. Number 2)

FIG. 7

DUPLEX 1:
Probe $T_r$    5'-$T_r$GTATTTGGAGGTCAGC$T_r$-3'
extension primer
(Sequence I.D. Number 4)

Probe F   3'-TTGCCATAAACC$F$CCAGTCG-5'
energy sink
(Sequence I.D. Number 5)

DUPLEX 2:
Probe $T_r$
5'-GCACCGTGC$T_r$GACCTCCAAA$T_r$ACCGTT-3'
extension primer
(Sequence I.D. Number 6)

Probe F
energy sink
(Sequence I.D. Number 7)   3'-$F$CGACTGGAGGTTTATG$F$-5'

FIG. 8

Extension primer (Sequence I.D. Number 8):

5'-TCCTAGGACCCCCTGCTCGTGTTACAGGCGGGGTTTTT-3';

Lagging probe (Sequence I.D. Number 9):
3'-LAATGTCCGCCCCAAAAA-5';

Extension primer (Sequence I.D. Number 10):
5'-GGTAT̲TGTGAGGATTCTTGT̲CAACAAG-3';

Lagging probe (Sequence I.D. Number 11):
3'-AAATAACACF̲CCTAAGAACAGTTGF̲-5'

FIG. 9

Leading Probe 1:   5'-TGGCTCAGTTTACTAGTGCCA-3'
extension primer (Sequence I.D. Number 12)

Leading Probe 2:   5'-GGAAAGCCCT̲ACGAACCACT̲GAACAAA-3'
extension primer (Sequence I.D. Number 13)

Lagging Probe 2:   3-'AATCGGGATGCTF̲GGTGACTTGT-5'
lagging probe (Sequence I.D. Number 14)

FIG. 10

METHOD FOR REDUCING NON-SPECIFIC PRIMING IN DNA AMPLIFICATION

FIELD OF THE INVENTION

This invention relates to a process for nucleic acid amplification in the absence of non-specific priming events. The invention also provides for detection of amplification by utilizing extension product elongation to displace a downstream probe. The invention further provides a homogeneous process for simultaneously amplifying and detecting a target sequence in a nucleic acid template. Products and apparatus related to the above-recited processes are also provided.

BACKGROUND

Recent development of the polymerase chain reaction (PCR) has provided an important tool for the detection of nucleic acid sequences present at low concentrations (Mullis, K. B. et al., U.S. Pat. No. 4,683,195 and 4,683,202). In PCR, a segment of target sequence having boundaries defined by two oligonucleotide extension primers, is amplified through repeated enzymatic cycles to provide additional templates for further amplification reactions. Accordingly, a small number of target sequences can be exponentially amplified and readily detected. A major limitation of PCR lies in the extensive generation of by-products produced as a result of non-specific priming events, e.g., random priming of the nucleic acid template and/or self priming of the extension primers. Thus, when a high number of amplification cycles are required to amplify a target sequence present at a relatively low concentration, the products of non-specific priming events significantly impede PCR sensitivity.

An additional, related limitation of PCR is the requirement for a separation step prior to detection of the amplified target. According to standard PCR conditions, separation of the amplified target sequence from the products of non-specific priming events is a prerequisite for detection of the amplified target sequence. The absence of a homogenous amplification reaction, i.e., a reaction in which amplification and detection take place in the same reaction vessel has been an obstacle in automating the PCR procedure. In addition, the requirement for a separation step also subjects the PCR mixture to potential contamination resulting from the separation procedure. The likelihood of contamination severely limits the potential application of PCR in routine clinical diagnosis.

Attempts have been reported to develop a homogeneous assay for amplification and detection. One such attempt is described in the procedure known as the ligase chain reaction (LCR, Beckman, K. C. and Wang, C. N., European Pat. No. 320,308). LCR is performed using two pairs of immediately adjacent and ligatable probes. The probes are amplified through repeated cycles of ligation. However, the probes can randomly ligate to each other to produce a background signal which is difficult to eliminate, thus reducing the sensitivity of detection.

SUMMARY OF THE INVENTION

The deficiencies in the prior art are overcome by the present invention which provides target amplification with substantially reduced amplification of non-target extension product. As a result, a truly homogenous process is achieved for simultaneously amplifying and detecting a target sequence in a nucleic acid template without the requirement of a separation step.

According to one aspect of the invention, a method for synthesizing extension products corresponding to a target sequence within a larger nucleic acid template is improved. A pair of primers for initiating polymerization dependent extensions to form the extension products are applied to the target sequence under conditions of polymerization dependent extension. These conditions substantially reduce or even prevent the synthesis of detectable amounts of non-target extension products. In the preferred embodiments, the extension conditions include the application of the primers to the template in the presence of an energy sink of sufficient binding affinity to at least one of the primers and in sufficient concentration so as to competitively inhibit binding of one of the primers to nontarget sites. The energy sink may be an oligonucleotide at least in part complementary to one of the primers and most preferably, the energy sink is a pair of oligonucleotides, one each complementary to the pair of extension primers. Detection of the extension product may be achieved according to various methods in which one or both of the primers and oligonucleotide are labelled.

According to another aspect of the invention, a homogeneous process for amplifying a target sequence in a nucleic acid and detecting the presence of the amplification without a separation step is provided. Two complementary strands of target sequence are treated with a pair of target-defining oligonucleotide primers, at least one of the primers being labelled, and with a labelled oligonucleotide reporter molecule, the reporter and primer producing a first signal when juxtaposed and a second signal when remote from one another. Extension conditions then are applied in repeated cycles to permit exponential amplification of the target sequence, after which at least one of the signals is measured. The reporter molecule may be adapted to prevent initiation from the reporter molecule of non-target extension. The extension conditions are adapted to reduce the likelihood of labelled reporter molecule from being juxtaposed with primer after repeated cycles of extension, and the conditions also may be such as to result in substantially-intact displacement of the reporter molecule. Alternatively, the conditions may be such as to result in some cleavage of labelled reporter molecule concurrent with the extension reaction, so long as the cleaved fragment contains the label and is displaced from its original position. The reporter molecule may be either an energy sink probe or a lagging probe.

According to still another aspect of the invention, a method for detecting a target sequence in a nucleic acid template is provided in which the template is treated with an extension primer and a lagging probe. Conditions then are applied to result in the formation of an extension product having a sequence corresponding to the target sequence. Initiation of extension product formation is by the extension primer. Elongation of the extension product is utilized to displace the lagging probe in substantially-intact condition. A signal generated by a reporting group attached to at least one of the lagging probe and extension primer results following displacement of the lagging probe and is measured.

In many of the methods of the invention, the extension primer may include an allele-specific recognition sequence which typically is positioned within two nucleotides of the 3' end of the extension primer.

According to still another aspect of the invention, a homogeneous process based upon strand-displacement amplification, is provided for detecting at least one target nucleic acid sequence. Two pairs of mutually complementary nucleic acid probes are provided in the presence of target nucleic acid. The probe pairs comprise a leading probe and a lagging probe, each being sufficiently complementary to the target nucleic acid sequence to hybridize therewith, the pairs of probes being constructed and arranged such that when hybridized to the target nucleic acid, the leading probes are juxtaposed relative to the 5' end of the lagging probes and separated therefrom by at least one nucleotide to form a gap between the leading and lagging probes of each probe pair. The probe pairs are then hybridized with the nucleic acid and subjected to conditions sufficient to permit the leading probe of each pair to elongate sufficiently to displace the lagging probe of each pair, thereby forming a replica of the target nucleic acid. Then, a reporting signal generated by the removal of lagging probes is detected. Preferably, the conditions applied result in the substantially-intact displacement of lagging probes. The reporting signal may be generated by a molecule attached to one of the leading and lagging probes, or both, the molecule being selected from the group consisting of a fluorophore, a chromophore, and a specific binding agent. Most preferably, the reporting signal is based upon the disruption of the interaction between a leading and a lagging probe. For example, one of the leading and one of the lagging probes may have fluorophores with overlapping emission and excitation wavelengths, and the reporting signal may be detected by measuring the disruption of the interaction between the overlapping emission and excitation wavelengths.

Alternatively, specific binding agents may be used to generate a signal dependent upon the relative proximity of probes. Specific binding agents include molecular entities such as enzymes, e.g., β-galactosidase, ribonuclease S and alkaline phosphatase. Each of these enzymes is capable of reassociating to form a functionally active enzyme following specific enzyme cleavage. This ability to reassociate and restore functional activity is referred to as intramolecular α complementation. For example, a specific binding enzyme agent may be cleaved into a first fragment and a second fragment. When the two fragments are proximately located to one another, the enzyme reassociates and is capable of catalyzing an enzyme reaction. For example, the first fragment may be covalently attached to the 3' end of an extension primer and the second fragment may be attached to the 5' end of an energy sink oligonucleotide which is complementary to the extension primer. When the extension primer is hybridized to the energy sink, the first and second fragments reassociate to form a functionally active enzyme. Upon introduction of an appropriate substrate and assay conditions, the enzyme will convert the substrate to a product capable of detection, e.g., a colorimetric substrate.

According to yet another aspect of the invention, a kit for use in the amplification of a target sequence in a nucleic acid template is provided. The kit includes a first oligonucleotide duplex including an extension primer for initiating the synthesis of an extension product corresponding to the target sequence in the nucleic acid template and a lagging probe complementary to the extension primer, wherein the lagging probe is adapted to prevent extension of non-target sequences. The extension primer may have a 3' end protruding beyond the 5' end of the lagging probe. The extension primer also may include an allele-specific recognition sequence at one of its ends. The extension primer and the lagging probe may be labelled in a complementing manner such that when they are juxtaposed, they produce a first signal that differs from a second signal produced when they are remote from one another. Most preferably, the kit includes a second oligonucleotide duplex including a second extension primer and a second lagging probe, wherein the first and second primers are target-defining primers.

Still another aspect of the invention provides an apparatus for simultaneously performing amplification of a target sequence in a nucleic acid template and detecting the presence of the amplified target in the absence of a separation step. The apparatus includes a probe container for containing an oligonucleotide duplex and a reaction vessel for containing a nucleic acid sample, the vessel is operatively linked to the probe container for receiving the duplex contained therein. The apparatus further has means for controlling mixing of the probes and sample and means for controlling the temperature of the reaction vessel. The apparatus also has a source for irradiating the reaction vessel and a means for detecting radiation emitted from the reaction vessel. Most preferably, the apparatus has a control mechanism which terminates the amplification reaction when a pre-designated level of radiation is detected by the means for detecting.

BRIEF DESCRIPTION OF THE DRAWINGS

FIG. 5A is a line graph illustrating the analysis of detecting different amounts of target HBV sequence at various amplification cycle. FIG. 5B is a bar graph illustrating the analysis of detecting different amounts of target HBV sequence at cycle 40.

FIG. 7 shows the extension primer, lagging probe and template used in connection with Example 1: Polymerization Dependent Strand-Displacement;

FIG. 8 shows pairs of extension primers and energy sink oligonucleotides used in connection with Example 3: Energy Transfer for Fluorophore Conjugated Probe Pairs;

FIG. 9 shows a four probe configuration used in connection with Example 5: A Homogeneous Assay for Detection of HBV Sequence; and FIG. 10 shows a three probe configuration used in connection with Example 5: A Homogeneous Assay for Detection of HBV Sequence.

DETAILED DESCRIPTION OF THE INVENTION

Figure 1:
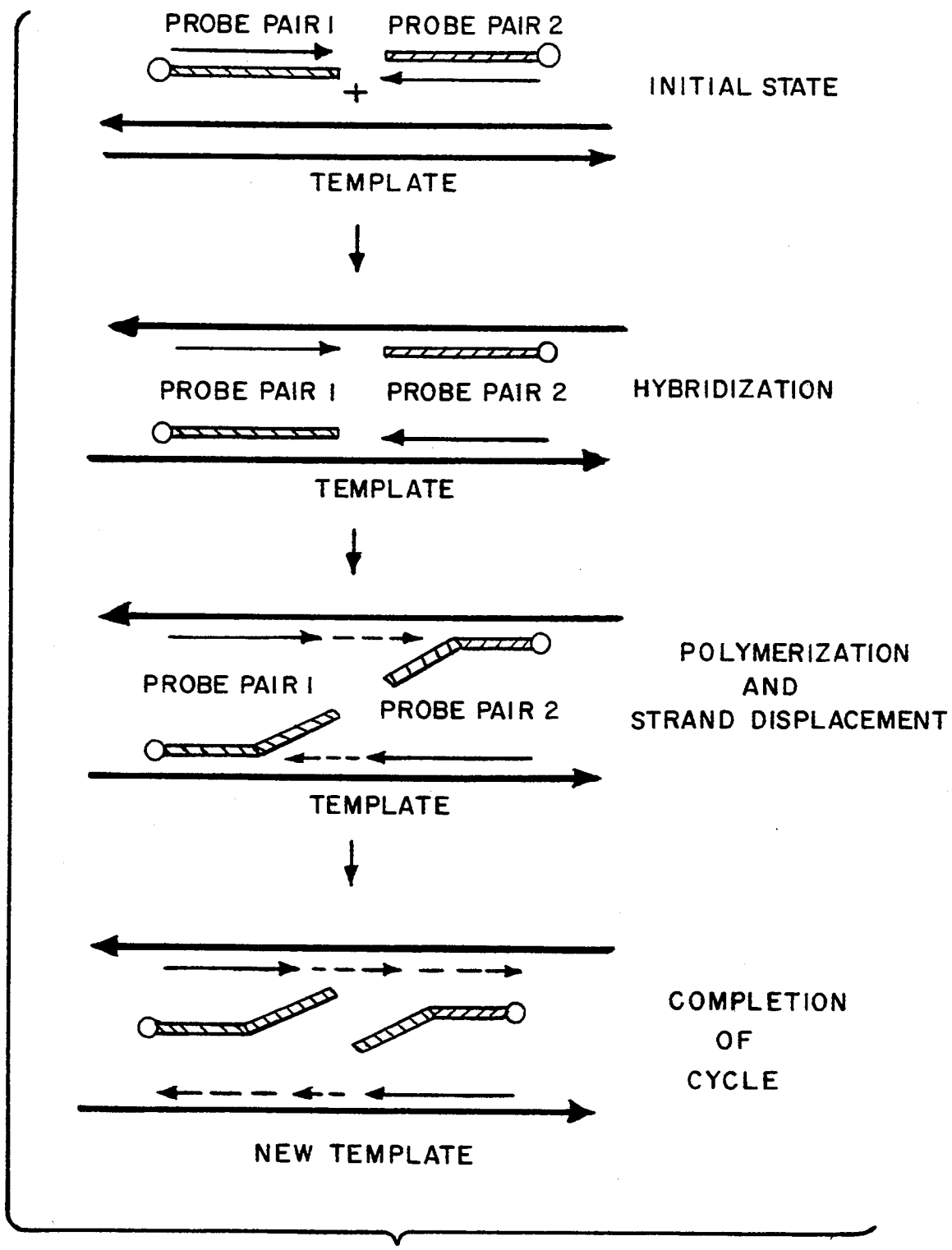
FIG. 1 is a schematic representation of the major steps constituting a cycle of polymerization-dependent strand-displacement amplification.

In a preferred embodiment, an improved method is provided for synthesizing complementary pairs of extension products corresponding to a target sequence in a nucleic acid template. The improvement comprises utilizing an energy sink oligonucleotide to inhibit nonspecific priming events.

As used herein, nucleic acid amplification refers broadly to a process for producing any particular nucleic acid sequence, i.e., the "target sequence", in amounts which are large compared to the amount initially present. One such process is described in U.S. Pat. No. 4,683,202, the contents of which are incorporated herein by reference. However, U.S. Pat. No. 4,683,202 does not address elimination of non-specific priming events occurring during nucleic acid amplification reactions; nor does the recited patent describe a homogeneous assay for simultaneously amplifying a target sequence and detecting the extension products corresponding thereto.

As in other amplification schemes, extension primers define the boundaries of the specific target sequence. The target sequence to be amplified may be only a fraction of a larger molecule or can be present initially as a discrete molecule, so that the specific sequence constitutes the entire nucleic acid. It is not necessary that the sequence to be amplified be present initially in a pure form; it may be a minor fraction of a complex mixture, such as a portion of the HBV gene contained in human genomic DNA (Example 5) or a portion of a nucleic acid sequence of a particular microorganism. The organism may constitute only a minor fraction of a particular biological sample.

Target defining oligonucleotide primers means primers, each complementary with a different strand of two separate complementary nucleic acid strands, such that when an extension product of one primer in the direction of the other primer is generated, that extension product can serve as a template for the synthesis of the extension product of the other primer. The target sequence is that portion of the nucleic acid between and including the sequence corresponding to the primers.

The phrase "non-specific priming events" refers to events which lead to amplification of a sequence on the template other than the target sequence. Non-specific priming events include reactions such as the random hybridization of an extension primer to a "non-priming sequence" of the template and self priming (inter and intra molecular reactions) by the extension primers. By "non-priming sequence" is meant a sequence on the template to which the extension primer may non-specifically hybridize, thereby initiating amplification of a non-target sequence. Non-specific priming events are a fairly common occurrence during amplification, due to the ability of the extension primer to hybridize to itself, other extension primers or to sequences on the template to which the primer is only partially complementary. Thus, as used herein, the term "non-target sequence" refers broadly to those sequences which are not target sequences, i.e., those sequences which are not the desired target or object of the amplification reaction. Such non-target sequences are unintentionally amplified by the non-specific hybridization of an extension primer to a non-priming sequence.

The nucleic acid template may contain more than one target sequence. Like the invention of U.S. Pat. No. 4,683,202, the present invention is useful for producing large amounts of one target sequence as well as for simultaneously amplifying more than one different target sequence located on the same or different nucleic acid templates. However, the present invention advantageously reduces to nondetectable amounts, non-specific priming events, thus making possible the simultaneous amplification and detection of a plurality of target sequences initially present in small amounts in the template.

Amplification relies upon hybridization of an "extension primer" to a specific "priming sequence" on the template. The terms "primer" or "extension primer" refer to an oligonucleotide, whether occurring naturally as in a purified restriction digest or produced synthetically, which is capable of acting as a point of initiation of synthesis when placed under conditions in which synthesis of a primer extension product complementary to a target sequence is induced. Thus the phrase, "capable of acting as a primer of an extension reaction" refers to the ability of an oligonucleotide to act as a point of initiation for extension product synthesis. Representative conditions for extension product synthesis are provided in the Examples.

As used herein, the term "oligonucleotide" refers to a molecule consisting of two or more deoxyribonucleotides or ribonucleotides, and preferably containing more than three nucleotides. The size of the oligonucleotide will depend on many factors, including the ultimate function or use of the oligonucleotide. Preferably, an oligonucleotide which functions as an extension primer will be sufficiently long to prime the synthesis of extension products in the presence of a catalyst, e.g., DNA polymerase, and deoxynucleotide triphosphates. The exact lengths of the primers will depend on many factors, including temperature, source of primer and use of the method. In diagnostic applications, for example, the oligonucleotide primer typically contains 15–25 or more nucleotides, depending on the complexity of the target sequence. For non-extension product applications, the oligonucleotide generally contains between 10–25 nucleotides. Shorter oligonucleotide generally require cooler temperatures to form sufficiently stable hybrid complexes with template.

To initiate "specific amplification", the extension primer hybridizes to a "priming sequence" on the template. Thus, the extension primer is designed to have a sequence which is "substantially complementary" to that of the priming sequence on the template. By "substantially complementary" between the primer and the priming sequence is meant that the two sequences must have a degree of nucleotide complementarity sufficient for the primer to hybridize to the priming sequence and act as a point of initiation for synthesis of an extension product.

Accordingly, the extension primer sequence is not required to be perfectly complementary to the priming sequence of the template. For example, a non-complementary nucleotide fragment may be attached to the 5' end of the primer, with the remainder of the primer sequence being substantially complementary to the priming sequence. Alternatively, non-complementary bases or modified bases can be interspersed into the extension primer, provided that base substitutions do not inhibit hybridization.

In addition to the specific priming sequence, the nucleic acid template may include "non-specific priming sequences" or "nonspecific sequences" to which the extension primer has varying degrees of complementarity. Thus, an extension primer may also be capable of hybridizing to non-specific priming sequences on the template, thereby initiating non-specific priming events which result in amplification of non-target sequences.

To a certain extent, the greater the sequence complementary between the extension primer and the priming sequence of the template, the less the likelihood for non-specific priming events. However, even exact complementarity between the primer and the priming sequence cannot eliminate hybridization of the primer to itself, other primers or probes, or to non-priming sequences on the template to which the primer may also be complementary.

To substantially reduce the possibility of non-specific priming events, the invention provides an energy sink oligonucleotide which competes with non-specific priming sequences for hybridization to the extension primer. Thus, the term "energy sink oligonucleotide" refers broadly to an oligonucleotide capable of hybridizing to an extension primer to prevent non-specific priming events. The energy sink is a molecular entity that is capable of competitively inhibiting the binding of a primer to nontarget nucleic acid sequences. The energy sink may be any molecule capable of performing this function, but preferably is an oligonucleotide of sufficient complementarity and in sufficient concentration so as to provide such competitive inhibition. It will be understood by one of ordinary skill in the art that the degree of complementarity and the concentration are interdependent variables. Thus, the energy sink may be perfectly complementary with the primer or alternatively imperfectly complementary with the primer, provided that the energy sink is present in sufficient concentration to competitively inhibit binding of the primer to nontarget sequences. There may even exist a nontarget sequence that is more complementary with the primer than is the energy sink, again, provided that the energy sink is present in sufficient concentration to competitively inhibit binding of the primer to nontarget sequences.

In the preferred embodiments, the energy sink is more complementary to the primer than to nontarget sequences and there is at least one energy sink molecule for every primer at the outset of the reaction. Most preferably, the energy sink is an oligonucleotide having at least ten consecutive bases perfectly complementary to a ten base sequence of a primer. In one preferred embodiment, the extension primer and energy sink oligonucleotide are initially hybridized to each other in a primer:energy sink duplex prior to initiation of the amplification reaction.

The primer and energy sink need not be fully contiguous, and in certain preferred embodiments are not. In one such embodiment the 3' terminal end of the primer protrudes or extends beyond the energy sink when the energy sink and primer are hybridized. This configuration precludes unintended extension of the primer in a 5'-3' direction when the primer is hybridized to the energy sink in a primer:energy sink duplex. In another such embodiment, the 3' end of the oligonucleotide is noncomplementary with the 5' end of the primer, so as to provide a mechanism for preventing extension from the 3' end of the energy sink when the energy sink hybridizes with target nucleic acid. It is necessary only that the primer and energy sink have sufficient overlapping regions to effect competitive inhibition as described above.

The energy sink is adapted to prevent initiation by the energy sink, of nontarget extension products. When the energy sink is an oligonucleotide, two types of initiation may occur. If the energy sink oligonucleotide hybridizes to target sequence, then extension may be in a 5' or 3' direction. If target duplication is in a 5'-3' direction from the primer, then nontarget extension from the energy sink oligonucleotide would also be in the 5'-3' direction. To prevent such nontarget extension, the 3' end of the energy sink oligonucleotide can be modified. Various modifications are well known to those of ordinary skill in the art and include 3'-dideoxy, 3'-phosphorylation, 3'-amino termination and the use of mismatching nucleotides at the 3' end of the energy sink, i.e., nucleotides which are not complementary to the target sequence. The second type of initiation that may occur is that resulting from the energy sink oligonucleotide hybridizing to nontarget sequences. Again, if conditions for (preferably) substantially only 5'-3' extension are applied, then the modifications of the 3' end of the energy sink oligonucleotide as described above will suffice.

As used herein, the term "primer:energy sink duplex" refers to the complex formed when the extension primer hybridizes to the energy sink oligonucleotide. Formation of the complex is a reversible process. Thus, under appropriate conditions, e.g., an increase in temperature followed by a reduction in temperature, the duplex may repeatedly dissociate and reassociate. It is not necessary that the extension primer and energy sink oligonucleotide have the same length. In one preferred embodiment, the 3' terminal of the extension product protrudes when the primer is hybridized to an energy sink oligonucleotide in a primer:energy sink complex.

The energy sink oligonucleotide may also be complementary to and thus capable of hybridizing to, a sequence in the nucleic acid template. However, the energy sink oligonucleotide is rendered incapable of acting as a primer for an extension reaction, such as by removing or modifying the 3' terminal hydroxy group. Alternatively, a nucleotide may be incorporated at the 3' terminal position which cannot base pair with a corresponding nucleotide on the template. These modifications to the 3' terminal of the energy sink oligonucleotide thus render the energy sink incapable of acting as a primer of an extension reaction.

As discussed above, the extension primer is capable of binding to (1) a specific priming sequence, (2) a non-specific priming sequence or (3) an energy sink oligonucleotide. Assuming that the extension primer is exposed to the template under conditions favorable to priming and extension, such as those conditions disclosed in the Examples, at least three different complexes are formed. The relative proportions of each complex are a function of concentrations (of the template, the extension primer and the energy sink oligonucleotide) and the free energy released for hybridization for each complex. The free energy released for hybridization of a primer to a complementary sequence to form a nucleic acid complex, e.g., duplex, may be analogized to the free energy released for a bimolecular chemical reaction. Accordingly, the magnitude of the free energy released following hybridization of two nucleic acid strands indicates whether the colliding nucleic acid strands are more or less likely to hybridize to one another. Thus, the free energy released following nucleic acid duplex formation reflects the degree of complementarity between the hybridizing molecules. The greater the complementarity between the component strands of the complex, the greater the free energy released will be for formation of the nucleic acid complex. Accordingly, complexes having greater degrees of complementarity will have a higher free energy released for hybridization and their formation will be favored over that of complexes having a lower free energy released for hybridization.

Hybridization of the extension primer to a specific priming sequence is energetically favored because the extension primer is designed to have a high degree of complementarity with the specific priming sequence. Hybridization of the extension primer to a nontarget sequence (leading to amplification of a non-target sequence) is unfavored because the degree of complementarity between the extension primer and the nontarget sequence will always be less than that between the extension primer and the energy sink oligonucleotide. Thus, the present invention provides target amplification with substantially reduced non-target extension product by providing an energy sink to eliminate possible hybridization of the extension primer to nontarget sequences. Because the energy sink is designed to be complementary to the extension primer, the free energy released for hybridization of an extension primer to its complementary oligonucleotide, e.g., energy sink, to form a primer: oligonucleotide duplex is more than the free energy released for hybridization of that primer to any nontarget sequence in the template.

Addition of the energy sink oligonucleotide in "sufficient concentration" to the amplification reaction mixture, prevents amplification of non-target sequences. As used in reference to the energy sink oligonucleotide concentration, the term "sufficient concentration" refers to an amount of energy sink oligonucleotide sufficient to prevent hybridization of the extension primer to non-specific priming sequences. Preferably, the energy sink oligonucleotide concentration will be at least equal to the extension primer concentration. More preferably, the concentration of the energy sink oligonucleotide will be in excess of 1-2 times the concentration of the extension primer. Preferably, the energy sink oligonucleotide is initially hybridized to the extension primer prior to admixing the extension primer with the template.

Amplification of a target sequence in a nucleic acid sample, in the absence of non-specific priming events, is accomplished by forming a reaction mixture containing a nucleic acid template, at least one extension primer and at least one energy sink oligonucleotide complementary to the extension primer. As used herein, the term "nucleic acid template" refers to purified or non-purified nucleic acid, provided that the nucleic acid contains or is suspected of containing the target sequence. Thus, the process may employ, for example, DNA, RNA or a DNA:RNA hybrid. The nucleic acid template is not limited to a DNA or RNA which is ultimately translated into a protein product, but may also include non-coding nucleic acid or non-coding nucleic acid sequences located between coding sequences. The target sequence may be identical to the template or may represent a portion of the template. Accordingly, a plurality of the same or different target sequences may be contained within a single template.

In general, the nucleic acid sample is double-stranded and it is necessary to separate the strands prior to extension product synthesis. In the Examples provided herein, heat denaturation is used to separate the strands of the nucleic acid sample. However, alternative agents are known in the art for separating nucleic acid strands, including chemical agents such as chaotropic agents, sodium hydroxide and hydrogen-bond disrupting agents. The primer and energy sink may be added as a duplex or as separate entities to the nucleic acid sample. If the primer and energy sink are added as a duplex, the steps taken to effect denaturation of the nucleic acid sample will likewise separate the primer:energy sink duplex into its respective strands.

Following strand separation, the reaction mixture is subjected to "hybridization conditions" to enhance hybridization of the extension primers to either priming sequences on the template to form a primer:template complex or to energy sink oligonucleotides to form a primer:energy sink complex. As used herein, the phrase "hybridization conditions" refers to those conditions known in the art for enhancing hybridization of substantially complementary sequences of nucleic acid. Representative standard conditions are provided in the Examples.

Once the extension primers are hybridized to the priming sequences of the template, the reaction mixture is subjected to "extension reaction conditions" to permit the extension primers to act as primers of an extension reaction, i.e., a polymerization reaction. It is not required that hybridization of the primer to the template and extension of the primer proceed under two distinct reactions. Thus, hybridization and extension may proceed simultaneously under reactions conditions which combine those conditions required for hybridization with those required for extension. As used herein, the phrase "extension reaction conditions" refers to those conditions known in the art for inducing synthesis of an extension product at the 3' end of an extension primer hybridized to a nucleic acid template. Thus, the addition of nucleotides and a catalyst, e.g., DNA polymerase, under conditions of known, controlled temperature, pH and ionic strength are encompassed within the phrase "extension reaction conditions". Representative extension reaction conditions are provided in the Examples.

The extension conditions are adapted to reduce the likelihood of a "reporter molecule" from being juxtaposed with the primer. As used herein, "reporter molecule" encompasses both energy sink oligonucleotides and lagging probes. The reporter molecule is optionally labelled (described below) with, for example, a fluorophore. As extension proceeds, primer availability is decreased due to its being incorporated into extension product. This reduces the amount of primer available to be juxtaposed adjacent a lagging probe on the same strand. As extension proceeds in repeated cycles, unlabelled extension product corresponding to the sequence of a lagging probe or energy sink is manufactured, which new product competes with labelled reporter molecules for juxtaposed binding with primer.

The catalyst for the extension reaction is generally a DNA polymerase, and is preferably a thermostable polymerase such as *Thermus aquaticus* or *Thermus thermophilus*. Under extension reaction conditions, the catalyst proceeds to sequentially add nucleotides to the 3' terminal of the extension primer, thereby synthesizing an extension product having a sequence which is complementary to the target sequence of the template. In the case of a double-stranded nucleic acid template, two extension products are initially synthesized, each extension product corresponding to one strand of the target sequence. The newly synthesized extension product represents a copy of the target sequence, which includes the primer sequence. The newly synthesized extension products are next separated from the template strand and are used as templates for synthesizing additional extension products.

The preferred method of strand separation is by heat denaturation. Thereafter, the single stranded extension products are used as templates in additional extension reactions. Completion of hybridization, extension and strand-separation constitutes one cycle of an amplification reaction. Thus, the concentration of extension product increases at an exponential rate with the completion of increasing amplification cycles. The extension product comprises the extension primer attached to and contiguous with, the amplified nucleic acid sequence complementary to the target sequence.

The invention further provides a method for detecting target sequences in a nucleic acid template by utilizing elongation of an extension product to displace a probe hybridized to the template at a position "downstream" of the sequence to which the extension primer is hybridized. As used herein, "upstream" and "downstream" are relative terms, used to describe the relative locations of a primer or probe hybridized to a nucleic acid template. For example, an extension primer for a particular target sequence, referred to as a "leading probe", would be described as being hybridized to the template at a position upstream, i.e., closer to the 3' end of the template, in relation to a "lagging probe", i.e., the probe displaced following elongation of the extension product.

The detection method of the invention is a homogeneous procedure which includes the steps of: (1) synthesis of an extension product; (2) displacement of a lagging probe and (3) detection of a change in a detectable signal generated by a reporting group attached to at least one of a leading probe and a lagging probe. As used herein, the term "homogeneous procedure" refers to a procedure which does not require a separation step for detection. Thus, extension product synthesis, probe displacement and detection are performed in a single reaction vessel. The probe which is displaced as a result of elongation of an extension product is referred to as the "lagging probe". Although the lagging probe hybridizes to the template, it is rendered incapable of acting as a primer of an extension reaction. Thus, the 3' terminal hydroxy group is either removed or modified to render the lagging probe inactive as a primer. Alternatively, the lagging probe may be designed to include a 3' terminal nucleotide which is not complementary to the template, thus rendering the lagging probe incapable of acting as an extension reaction primer.

Synthesis of the extension product has previously been described. The second part of the detection method, i.e., probe displacement, is described herein.

According to the detection method, a reaction mixture is formed, and extension primers are hybridized to the template under controlled hybridization conditions as previously described. In one preferred embodiment, the energy sink oligonucleotides are complementary to both extension primers and to target sequences on the template. However, although capable of hybridizing to the template, the energy sink oligonucleotides are incapable of acting as primers of an extension reaction. Thus, in a most preferred embodiment, the energy sink oligonucleotides serve a dual role: (1) as energy sink molecules for eliminating non-specific priming events and (2) as lagging probes useful in performing a homogeneous detection process. This embodiment is schematically depicted in FIG. 1.

In yet another embodiment, the lagging probes are not identical to energy sink oligonucleotides, i.e., are not substantially complementary to the extension primer, but are "associated" with particular extension primers in a "detection probe pair". The detection probe pair comprises a leading probe and a lagging probe, wherein each member probe of the pair hybridizes to the same template strand. Thus, the primer and probe are "associated" in that elongation of the extension primer displaces the lagging probe from the template. When hybridized to the template, the 3' terminus of the extension primer is preferably separated from the 5' end of the lagging probe by at least one nucleotide but by no more than 20 nucleotides.

The detection method also provides a reporting group attached to at least one of the leading probe and the lagging probe. Preferably, the detection method utilizes at least two different reporting groups attached to two different primers or probes. The different reporting groups are labels which interact with one another to either generate or quench a signal emitted by one of the reporting groups. The labels may be fluorophore labels, e.g., fluorescein, rhodamine, eosin or Texas Red, attached to different probes. Alternatively, the reporting groups may be specific binding agents such as enzymes, e.g., $\beta$-galactosidase, ribonuclease S and alkaline phosphatase. Generally, specific binding enzyme agents are capable of reassociating to form a functionally active enzyme following enzyme cleavage or other dissociation. This ability to reassociate and restore functional activity is referred to as intramolecular $\alpha$ complementation. When the two fragments are proximately located to one another, the enzyme reassociates and is capable of catalyzing an enzyme reaction. Thus, for example, the first fragment may be covalently attached to the 3' end of an extension primer and the second fragment may be attached to the 5' end of an energy sink oligonucleotide which is complementary to the extension primer. When the extension primer is hybridized to the energy sink, the first and second fragments reassociate to form a functionally active enzyme. Upon introduction of an appropriate substrate and assay conditions, the enzyme will convert the substrate to a product capable of detection, e.g., a colorimetric substrate.

Regardless of whether the reporting groups are positioned on probes which are initially hybridized to one another (e.g., a primer:energy sink duplex) or are positioned on probes which are hybridized to a common template strand (e.g., a detection probe pair), the requirement for homogeneous detection is the same. Displacement of the lagging probe from the template must change the interaction of the reporting groups. Thus, the reporting groups may be within each other's quenching distance prior to elongation (no signal), such that diplacement causes the reporting groups to separate from one another, thereby generating a signal. Accordingly, the labels function in a complementing manner to produce a complementary signal. By complementary signal is meant a signal, the generation of which is dependent upon the juxtaposition of the labelled primer and a labelled reporter molecule (energy sink or lagging probe). Juxtaposition means brought in close spatial relationship either as a result of the hybridization of the primer to the reporter molecule or as a result of the primer and reporter molecule hybridizing adjacent one another on the same strand of target nucleic acid.

For example, a first fluorophore is attached to the extension primer (leading probe) near its 3' terminal and a second fluorophore is attached to the lagging probe near its 5' terminal, to provide first and second fluorophore within quenching distance of one another. Accordingly, if the first fluorophore is a donor fluorophore having an emission spectra which overlaps with the absorption spectra of the second (acceptor) fluorophore, the light emitted by the donor fluorophore is absorbed by the acceptor fluorophore and is quenched when the leading probe and lagging probe are hybridized to the template. When the lagging probe is displaced from the template during elongation of the extension product, a signal is generated. Thus, the invention also provides a homogeneous detection method, i.e., detection in the absence of any separation step. In contrast, traditional methods of detection such as autoradiography rely upon electrophoretic separation of reacted and unreacted reporting groups, e.g., radiolabeled-probes, to determine whether amplification has occurred.

In the preferred embodiment of the invention, the first fluorophore is attached to the extension primer and the second fluorophore is attached to its complementary energy sink oligonucleotide, such that the two fluorophores are within quenching distance of one another when the extension primer and energy sink are hybridized to one another in duplex form. The overlap of emission spectrum of the first fluorophore (donor fluorophore) and the excitation spectrum of the second fluorophore (acceptor fluorophore) allows energy transfer between the two fluorophores. Accordingly, a change in signal due to disruption of the energy transfer, is generated when the duplex is denatured or dissociated such as for example, during the first step of an extension reaction. Following generation of an extension product, the reaction mixture is subjected to conditions which allow complementary strands of nucleic acid to hybridize. Thus, an equilibrium is established in which fluorophore-labeled extension primer and energy sink hybridize to one another or alternatively, hybridize to the amplified target sequence, i.e., extension product. A change in signal is not generated if the primer:energy sink duplex is reformed; a change in signal is generated if at least one type of the fluorophore-labelled oligonucleotides hybridizes to the amplified target. The change in signal becomes more significant as the number of amplification cycles increases. This result is due to the availability of a greater concentration of amplified target, which shifts the equilibrium in favor of fluorophore-labelled oligonucleotide binding to amplified target.

In one preferred embodiment, the invention is used to detect allale-specific sequences present in the nucleic acid template. According to this embodiment, at least one extension primer includes an allale-specific recognition site located near its 3' terminus. As used herein, the term "allele-specific recognition site" refers to a sequence which is either complementary or non-complementary to an allele sequence located in a priming sequence of the template. The allele specific recognition site can be a single or multiple nucleotide substitution or deletion. Preferably, the recognition site is positioned one or two nucleotides from the 3' end of the extension primer to disrupt hybridization between the primer and priming sequence when the allele specific recognition site is non-complementary to the allele sequence in the template. Thus, under mismatching conditions, the primer will not initiate primer extension, a lagging probe having an attached acceptor fluorophore attached will not be displaced and a signal will not be generated.

In addition to the above-described methods, the invention provides oligonucleotide duplexes, pairs of duplexes, and detection probe pairs, wherein the oligonucleotides comprising the duplexes are optionally labelled with reporter groups. The oligonucleotide duplex comprises an extension primer for initiating the synthesis of an extension product corresponding to a target sequence in a nucleic acid template and an energy sink oligonucleotide complementary to the extension primer. The energy sink oligonucleotide may hybridize to a non-priming sequence on the template but is incapable of acting as a primer of an extension reaction. The pairs of duplexes define the boundaries of the target sequence in the template. Thus, use of pairs of duplexes in the above-disclosed improved amplification reaction results in amplification of the target sequence in the absence of amplification of non-target sequences in the template. A reporter group, such as a fluorophore, is optionally attached to at least one of the extension primer and the energy sink oligonucleotide in the primer:energy sink duplex.

In addition, the invention provides an apparatus for simultaneously performing amplification of a target sequence in a nucleic acid template and detecting the presence of the amplified target in the absence of a separation step. The apparatus comprises, (1) a probe container for containing oligonucleotide primers and/or probes; (2) a reaction vessel for containing a nucleic acid sample, wherein the vessel is operatively linked to the probe container to permit automated transfer of the probe container contents to the reaction vessel; (3) a controller for mixing the probes and sample; (4) a temperature controller for controlling the temperature of the reaction vessel; (5) an irradiation source; and (6) a detector for detecting radiation emitted from the reaction vessel. In the preferred embodiment, the reaction vessel is the well of a multi-well microtiter plate. Generally, the irradiation source is a device capable of generating photons of desired wavelength. Such devices are well known to those of ordinary skill in the art, are readily commercially available from numerous sources and include for example tungston lamps or ionizing laser lamps. The detector is a device capable of converting photon energy into an electrical signal. Again, such devices are well known to those of ordinary skill in the art, are readily commercially available from numerous sources and include for example photomultiplier tubes or semiconductor-based photon detectors.

Preferably, the apparatus further includes a data processor for processing the signal data received by the detector. In a most preferred embodiment, the apparatus includes a control mechanism which terminates the amplification reaction when a pre-designated level of radiation, corresponding to a pre-selected level of amplification, is detected by the detector. Thus, the apparatus provides for "on-line" monitoring of the amplification reaction in a manner analogous to the on-line monitoring of fermentation products used for large scale recombinant protein synthesis. Accordingly, use of the homogeneous amplification and detection method in combination with the apparatus disclosed herein eliminates contamination of the reaction vessel by eliminating the need to sample the mixture to determine the degree to which target sequence amplification has occurred.

Figure 11:
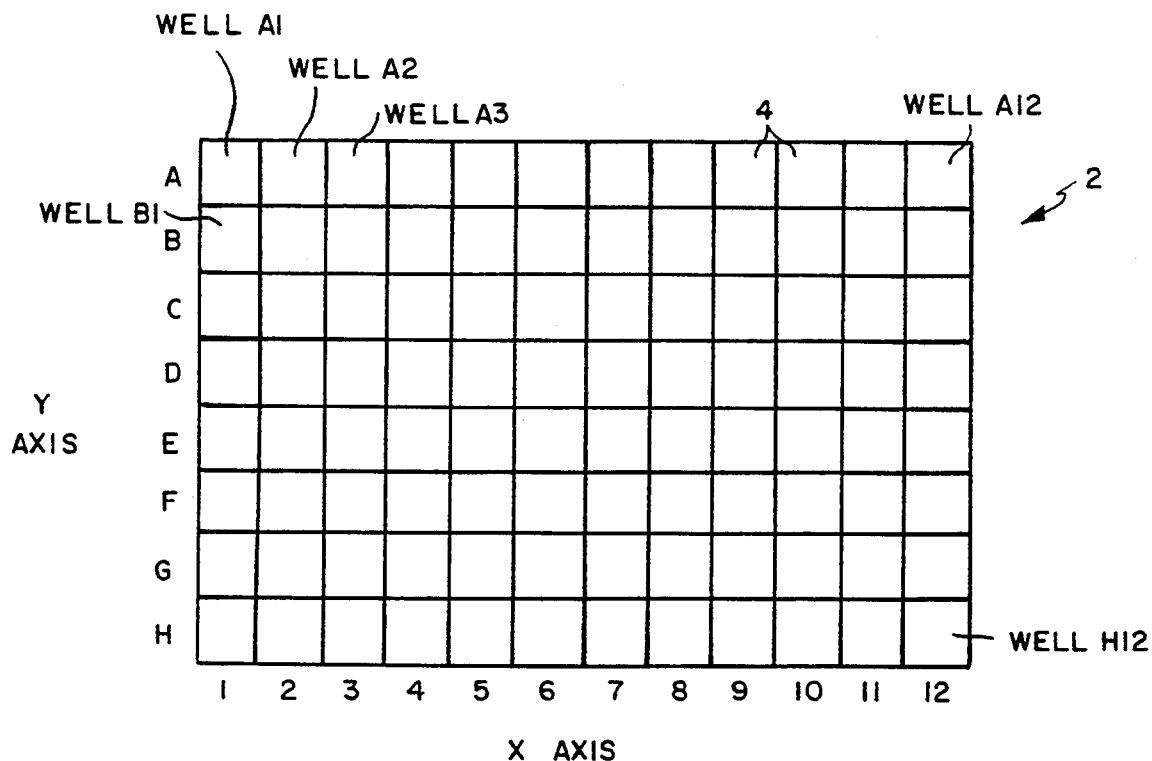
FIG. 11 illustrates the configuration of a microtiter plate utilized in the present invention.

As previously stated, in the preferred embodiment of the invention, the reaction vessel is the well of a multi-well microtiter plate. Although other multi-well microtiter plates could be utilized, FIG. 11 illustrates the configuration of the microtiter plate 2 which is utilized in one embodiment of the invention. The microtiter plate 2 contains ninety-six wells 4 that are configured in a rectangular fashion with twelve columns of wells along its X axis, i.e. columns 1-12, and eight rows of wells along its Y axis, i.e. rows A-H. The use of the multi-well microtiter plate enables a plurality of reactions to be conducted simultaneously, each reaction being confined within one well 4 of the microtiter plate 2.

In the descriptions of the methods and apparatuses for practicing the present invention which are provided below, in the preferred embodiment donor and acceptor fluorophores are utilized for generating a change in fluorescence, relating to the level of amplification that has occurred, based upon disruption of energy transfer. It should be understood that various other fluorophore configurations can be utilized for generating changes in fluorescence indicating the level of amplification in other ways. However, the methods and apparatuses described below can be utilized to detect fluorescence change indicating amplification regardless of how that change is accomplished.

Figure 12:
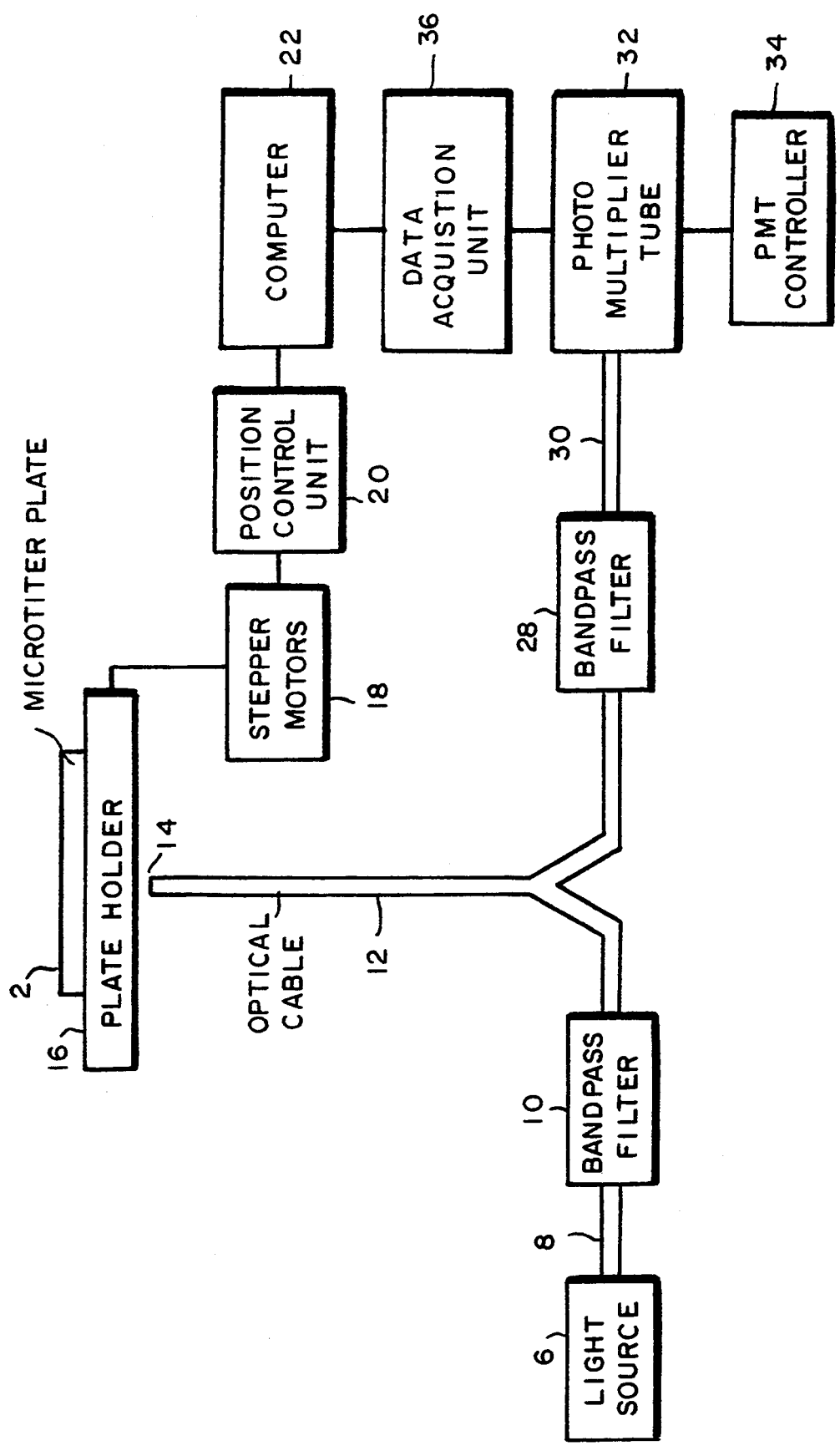
FIG. 12 is a block diagram of one embodiment of the detector apparatus of the present invention.

FIG. 12 illustrates one embodiment of an exemplary detector apparatus utilized to practice the present invention. Light source 6 is provided which is capable of generating photons of a desired wavelength to excite emissions from a donor fluorophore. It is preferable to utilize a lamp that provides incident light or, alternatively, a laser based light source can be utilized. In the preferred embodiment of the invention, the light source 6 is a one hundred fifteen watt tungsten halogen lamp, Cuda Products Corp. (Jacksonville, Fla.) model no. 1-150. This tungsten halogen lamp generates photons at a broad range of wavelengths. The photons generated by the light source 6 pass through an optical cable 8 into a bandpass filter 10. The bandpass filter 10 transmits only photons within a given wavelength band. The passband of the bandpass filter 10 is selected to filter out photons at wavelengths above and below the desired excitation wavelength for the donor fluorophore. In the preferred embodiment of the invention, the donor fluorophore is fluorescein or fluorescein isothiocyanate (hereafter FITC). Emissions are generated from FITC in response to excitation photons having wavelengths in the range of 490 nm. Therefore, bandpass filter 10 is chosen to pass photons having wavelengths ranging from 470 nm to 510 nm. Bandpass filter 10 filters out photons at wavelengths that would excite the acceptor fluorophore, as well as wavelengths that might excite emissions from other materials that could be close to the acceptor fluorophore's emission wavelength. In this manner, bandpass filter 10 reduces interference with the fluorescence emitted by the acceptor fluorophore. The donor fluorophore FITC emits photons having an emission maximum at approximately 520 nm. The FITC emission spectrum extends to at least 590 nm. An acceptor fluorophore is selected that has an excitation spectrum that overlaps with the FITC emission spectrum to achieve energy transfer from FITC to the acceptor fluorophore. In the preferred embodiment of the invention, the acceptor fluorophore is Texas Red which is responsive to photons in the range of 590 nm and has an emission spectrum in the range of 630 nm.

The filtered light from bandpass filter 10 is transmitted into an optical cable 12. The optical cable 12 terminates at an emitting/receiving end 14 which is positioned below the microtiter plate 2. The emitting/receiving end 14 of the optical cable 12 acts as a radiation source for emitting photons onto the reactions contained within the wells 4 (FIG. 11) of the microtiter plate 2.

As was previously stated, separate reactions can be conducted within each of the wells 4 (FIG. 11) of the microtiter plate 2. In order to separately detect the amount of amplification that has been produced by each of these reactions, the detection apparatus is provided with a means for positioning the emitting/receiving end 14 of the optical cable 12 below each well 4 (FIG. 11) of the microtiter plate 2. The positioning apparatus includes, for example, a plate holder 16 that supports the microtiter plate 2. The plate holder 16 is connected to a pair of stepper motors 18, which change the position of the plate holder 16, and consequently the microtiter plate 2, independently along both its X and Y axes relative to the emitting/receiving end 14 of the optical cable 12. The stepper motors 18 are responsive to a position control unit 20 which issues commands to the stepper motors 18 to control the positioning of the plate holder 16. In this manner, the position of the plate holder 16 can be adjusted to position each well 4 (FIG. 11) of the microtiter plate 2 above the emitting/receiving end 14 of the optical cable 12. The position control unit 20, in turn, is controlled by commands issued from a computer 22. A software program executed by the computer 22 issues commands to the position control unit 20 to vary the position of the plate holder 16 relative to the open end 14 of the optical cable 12 to enable detection of the status of the reactions conducted within each well 4 of the microtiter plate 2.

Figure 13:
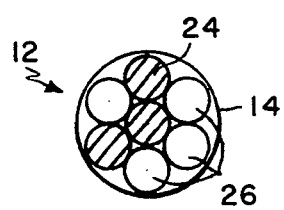
FIG. 13 illustrates the physical construction of a bifurcated optical cable utilized by the present invention.

In the preferred embodiment of the invention, a bifurcated fiber optic type cable is used wherein, as shown in FIG. 13, the optical cable 12 includes both emitting fibers 24 and receiving fibers 26 within the same optical cable 12. Although two separate optical cables could be utilized that separated the emitting fibers from the receiving fibers, the use of a bifurcated fiber optic cable is desirable because it is simpler to physically locate one optical cable directly under a given well 4 rather than attempting to position two cables under a well. As a result, the single optical cable 12 can be more precisely positioned below a given well, thereby increasing the accuracy of the information received from the well.

In the embodiment of the invention illustrated in FIG. 12, the emitting/receiving end 14 of the optical cable is positioned below the microtiter plate 2 rather than above it. This positioning is optimal because it eliminates a potential source of error caused by an overlayer of oil on the top surface of the reactants within the wells or covers over the wells. However, testing has shown that the emitting/receiving end 14 of the optical cable 12 could alternatively be positioned above the microtiter plate 2 without suffering any substantial decrease in system performance.

As described above, the degree of amplification within a given reaction can be determined by analyzing the level of fluorescence emitted from the reaction at the acceptor fluorophore's emission wavelength. In order to detect the level of fluorescence within any selected well 4 (FIG. 11) of the microtiter plate 2, the emitting/receiving end 14 of the optical cable 12 is positioned below the selected well 4 by moving the microtiter plate 2. Radiation emitted from a reaction taking place within the selected well 4 is transmitted through the receiving fibers 26 (FIG. 15) within optical cable 12 to a bandpass filter 28. Bandpass filter 28 transmits only light that has a wavelength corresponding to the emission spectra of the acceptor fluorophore. As previously stated, in the preferred embodiment of the invention, the acceptor fluorophore is Texas Red which has an emission maximum of approximately 630 nm. Therefore, bandpass filter 28 is selected to transmit photons at wavelengths ranging from 610 nm to 650nm.

The filtered signal from bandpass filter 28 is transmitted to a photomultiplier tube (PMT) 32 through an optical cable 30. The photomultiplier tube is responsive to signals having wavelengths ranging from 610 nm to 650 nm. Photomultiplier tube 32 is a type of photon detector which, when photons of light are incident upon it, generates electrical signals indicative of the intensity of the photons of incident light striking the photon detector. Although other types of photon detectors could be used, the photomultiplier tube 32 is utilized because it provides desirable performance characteristics. A PMT controller 34 controls various performance characteristics and operating conditions of the photomultiplier tube 32 independent of the operation of the remainder of the system. In the preferred embodiment of the invention, a Hamamatsu (Bridgewater, N.J.) model no. R1477 is utilized as photomultiplier tube 32.

As stated above, photomultiplier tube 32 generates electrical signals that are related to the intensity of the incident signals. Since the light signals incident upon the photomultiplier tube 32 represent the level of fluorescence in the selected well 4 (FIG. 11), the electrical signals generated by the photomultiplier tube 32 are similarly indicative of the intensity of the acceptor fluorophore emissions within the selected well 4 (FIG. 11). These electrical signals are transmitted from the photomultiplier tube 32 to a data acquisition unit 36. Data acquisition unit 36 acts as an interface between photomultiplier tube 32 and a computer 22. Data acquisition unit 36 performs various interface operations that convert the electrical signals transmitted from photomultiplier tube 32 into a digital format that is read by computer 32. These interface operations are well known to those skilled in the art and include analog to digital conversion of the electrical signals, as well as any buffering necessary to synchronize the electrical signals with an internal clock of the computer 22.

Specific implementations of the detection apparatus illustrated in FIG. 12 can be accomplished in a number of different ways that are known to those skilled in the art. A detection system, excluding the computer 22, has been manufactured for applicants by Cambridge Technology, Inc., 23 Elm Street, Watertown, Mass. 02172-2821. In the preferred embodiment of the invention, the computer 22 is an IBM compatible personal computer which is connected to the remainder of the detection apparatus via an RS-232C, fully bidirectional, 9600 baud interface. Other computers and interfaces may, of course, be used.

As previously stated, fluorophores other than those described above can be utilized in practicing the present invention. Therefore, fluorophores can be utilized that have different excitation and emission wavelengths. When different fluorophores are utilized, the apparatus illustrated in FIG. 12 will be chosen to correspond to the use of those fluorophores. The light source 6 and bandpass filter 10 will be chosen to provide photons at the excitation wavelength of the donor fluorophore. Similarly, bandpass filter 28 and photomultiplier tube 32 will be chosen to respond to the emission wavelength of the acceptor fluorophore.

Figure 14:
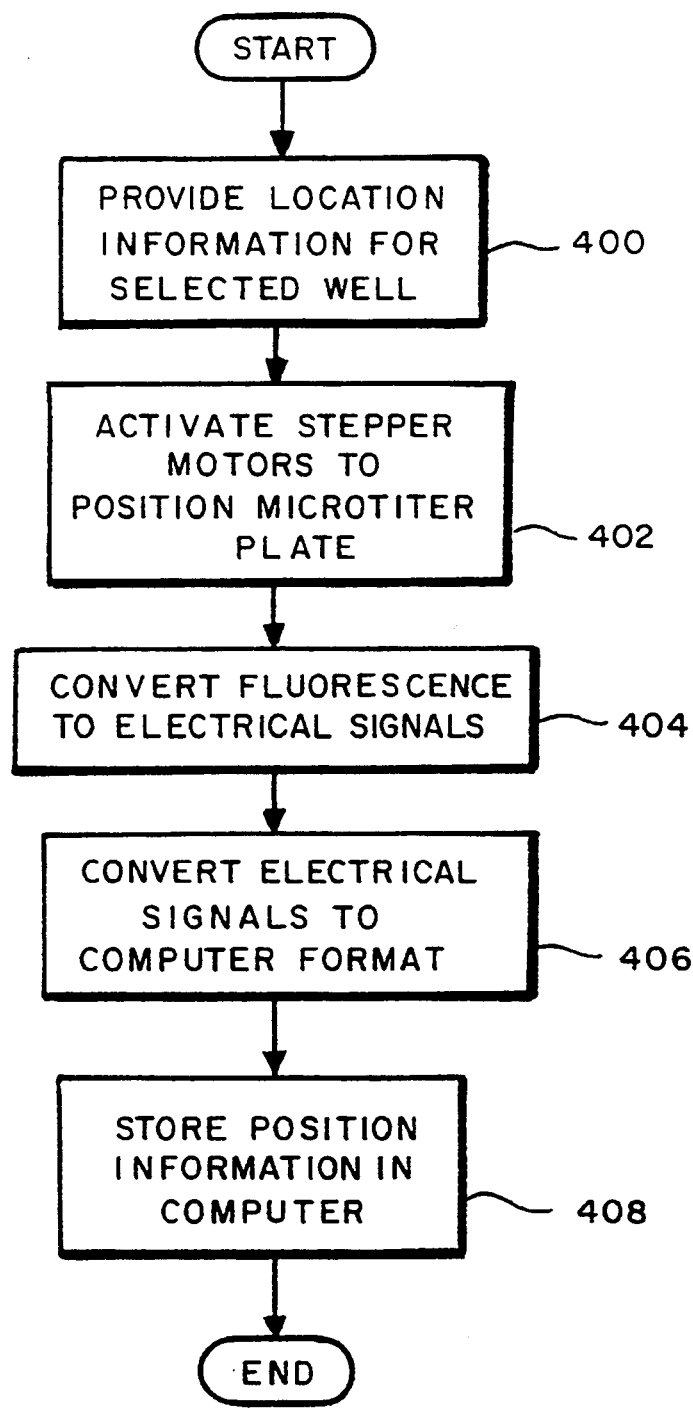
FIG. 14 is a flowchart illustrating a method by which the detection apparatus of the present invention determines the fluorescence level within each well in the microtiter plate.

The detection apparatus illustrated in FIG. 12 provides data that enables a program executing on computer 22 to monitor the degree of amplification which has occurred within each of the wells 4 (FIG. 11) of the microtiter plate 2. Reference is made to FIG. 14 for a brief description of the method by which the apparatus illustrated in FIG. 12 is utilized to accomplish detection. When any given reaction is to be examined, the program first identifies the well 4 (FIG. 11) in which the reaction is taking place. In step 400, computer 22 provides location information for the selected well 4 (FIG.

11) to the position control unit 20. In step 402, the position control unit 20 activates stepper motors 18 to position the selected well 4 (FIG. 11) above emitting-/receiving end 14 of the optical cable 12. Once the selected well 4 is positioned in this manner, the radiation photons emitted by the acceptor fluorophore is transmitted through receiving fibers 26 (FIG. 13) of optical cable 12, bandpass filter 28 and optical cable 30 to photomultiplier tube 32. In response to this incident radiation, photomultiplier tube 32 generates electrical signals indicating the intensity of the acceptor emission in step 404. In step 406, these electrical signals are converted by the data acquisition unit 36 into a format compatible with the computer 22. In step 408, the computer 22 stores data indicating the amount of amplification that has taken place in the selected well 4 (FIG. 11).

As described above, the reactions that result in the desired amplification are brought about through a series of heating and cooling cycles. The detection apparatus shown in FIG. 12 does not include any apparatus for heating or cooling the microtiter plate 2. Therefore, the heating and cooling of the microtiter plate 2 is accomplished through the use of other apparatus. Consequently, when it is desired to determine the level of amplification which has taken place at any given point in the reaction process, the microtiter plate 2 is removed from the heating/cooling apparatus (not shown, as conventional equipment may be employed) and transferred to the detection apparatus shown in FIG. 12.

Figure 15:
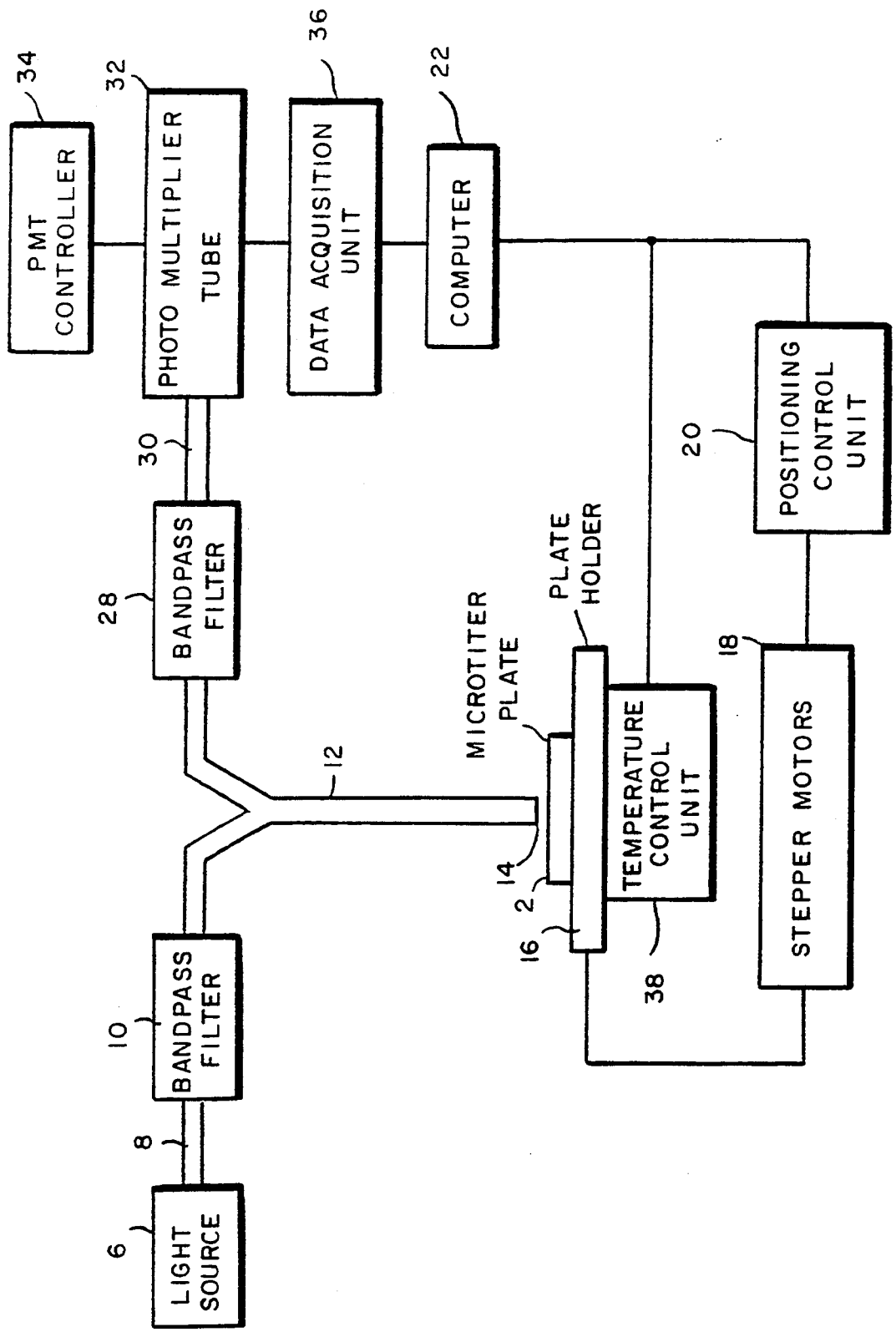
FIG. 15 is a block diagram of one embodiment of the amplification/detection apparatus of the present invention.

FIG. 15 illustrates an alternate embodiment of the present invention wherein the detector apparatus is combined with apparatus for heating and cooling the reactions within the microtiter plate 2. This embodiment contains each of the elements of the detector apparatus illustrated in FIG. 12, and like elements have been assigned the same reference characters. Additionally, the system illustrated in FIG. 15 also includes a temperature control unit 38 that controls the temperature of the reactions occuring within the microtiter plate 2.

Figure 16:
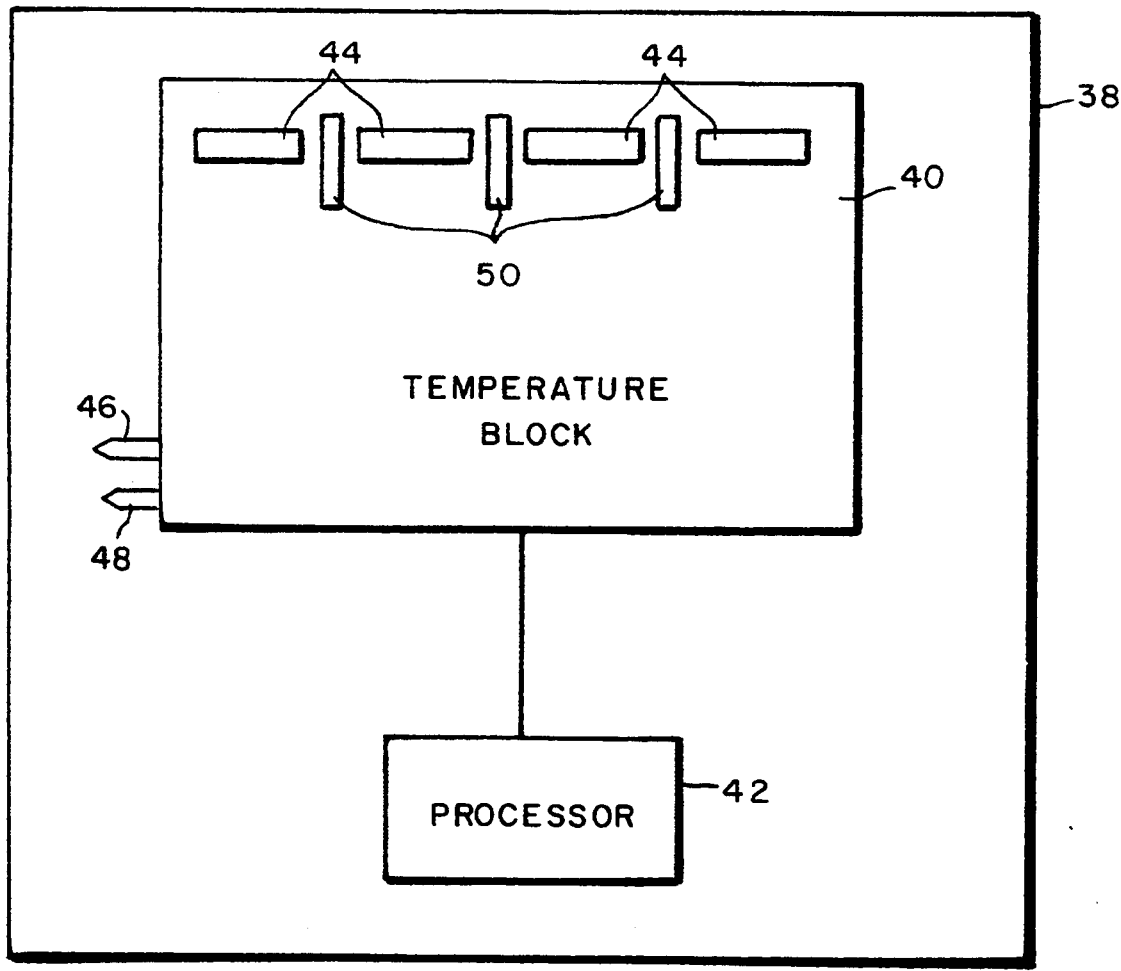
FIG. 16 is a block diagram of a temperature control unit utilized by the amplification/detection apparatus of the present invention.

The temperature control unit 38 is illustrated in FIG. 16 and includes a temperature block 40 and a processor 42 for controlling the operation thereof. Temperature block 40 includes a plurality of heating coils 44 for raising the temperature of the temperature block. Temperature block 40 also includes an inlet valve 48 for controlling the flow of a cooling fluid, which may be water, into the temperature block 40 to reduce the temperature thereof. An outlet tap 48 is also provided to allow for drainage of the water from temperature block 40. A plurality of thermocouplers 50 are provided to measure the temperature within the temperature block 40. The temperature block is controlled by processor 42 which monitors the thermocouples 50 to determine the temperature of the temperature block 40. Processor 42 controls heating of the heating coils 44 as well as the flow of cooling fluid through input valve 46 in order to control the temperature of temperature block 40. An example of a temperature unit 38 that provides each of the above-described features is manufactured by Techne Incorporated, 3700 Brunswick Pike, Princeton, N.J. 08540 under the name "Dri-Plate Cycler" TM. Other types of commercially available temperature control units can also be utilized.

In the system illustrated in FIG. 15, processor 42 (FIG. 16) of temperature control unit 38 is coupled to and controlled by computer 22. A program executing on computer 22, as is more fully described below, executes a series of heating, cooling and detection steps until the system determines that the desired amount of amplification has been achieved. Consequently, the apparatus illustrated in FIG. 15 is self-contained and performs each of the steps necessary to achieve amplification, as well as detection of the amount of amplification achieved.

The apparatus illustrated in FIG. 15 also differs from the detection apparatus illustrated in FIG. 12 in one other respect. Due to the positioning of temperature unit 38, emitting/receiving end 14 of the optical cable 12 cannot be positioned below microtiter plate 2 because temperature unit 38 would block the fluorescence emitted from microtiter plate 2. Consequently, emitting-/receiving end 14 of optical cable 12 is positioned above microtiter plate 2. As previously stated, positioning emitting/receiving end 14 of optical cable 12 above microtiter plate 2 does not negatively impact the performance of the detection apparatus.

Detection Method

A description is now provided of the manner in which computer 22 is programmed to control the apparatus illustrated in FIG. 12 to implement a detection method for detecting the amount of amplification that has occurred within each of the wells of microtiter plate 2. Before beginning the execution of the detection program on computer 22, a series of initialization steps are conducted to determine certain testing parameters and to initialize the system. First, four types of wells are chosen within the microtiter plate 2 to provide various types of calibration information utilized during the execution of the detection program. Any of the wells 4 (FIG. 11) of the microtiter plate 2 can serve as one of these calibration wells. The four calibration wells include (1) a reference well, (2) a control well, (3) a standard well and (4) a background well; the purpose of each of these calibration wells is described below. A single or multiple wells can be chosen for each type of calibration well. Once a given well is selected to serve as a calibration well, the "well address" of the selected well is manually (or otherwise) inputted into computer 22 along with a label indicating which of the calibration wells is assigned to that address. The well address is defined by its X and Y coordinates (see FIG. 11). The well address for each of the calibration wells is stored within the computer 22 for later use in the detection program.

The background well is filled with only water. It is utilized by the detection program to indicate the level of light present at the acceptor's emission wavelength from background sources, i.e. sources other than the acceptor fluorophore. As is more fully described below, the level of fluorescence within the background well is subtracted from the fluorescence level detected within each well to provide a true fluorescence level that indicates the fluorescence emitted solely by the acceptor fluorophore.

The reference well contains all the reactants except for the enzymes necessary for amplification. As a result, the fluorescence emitted from the reference well indicates the maximum amount of fluorescence because its fluorescence will not be reduced due to any amplification. As is more fully described below, the reference well provides a base fluorescence value that is utilized to determine the percentage reduction of fluorescence that has occurred in any given well due to amplification.

The control well contains no target molecules. Therefore, any change in fluorescence in the control well occurs solely as a result of non-specific amplification. As is more fully described below, the level of fluorescence in the control well is utilized to determine when the amount of non-specific amplification has reached an undesirably high level.

The standard well contains a known amount of target molecules and therefore provides a basis for quantifying the amount of amplification that corresponds to a given percentage change in fluorescence. The percentage change of fluorescence caused by a given quantity of amplification will vary logarithmically depending upon the number of target molecules present in the initial reaction vessel. Therefore, the percentage change in fluorescence of a reaction vessel having an unknown quantity of target molecules does not indicate the exact extent of amplification which has occurred. However, since the standard well contains a known number of target molecules, the extent of amplification that correspond to its percentage reduction in fluorescence can be established through prior experimentation. As is more fully described below, the detection program utilizes the standard well to determine when the reaction process has reached the desired level of amplification by determining when the percentage change of fluorescence within the standard cell reaches the percentage corresponding to the desired quantity of amplification.

Two additional pieces of information are also input into computer 22 prior to beginning execution of the detection program. Each of these pieces of information is also stored within computer 22 and provides a parameter for determining when the reaction steps are complete. These parameters can be set to any values chosen by an operator of the detection apparatus illustrated in FIG. 12. First, a threshold value is stored which defines a percentage change of control well fluorescence that, if reached, indicates that the amplification process should be terminated. This threshold is chosen to indicate that an undesirable level of non-specific amplification has occurred. If the level of non-specific amplification surpasses the threshold level, it indicates that the change in fluorescence due to amplification cannot be distinguished from change in fluorescence due to non-specific amplification. If this condition occurs, the reaction process should be aborted. Second, a threshold value is selected for the percentage change in fluorescence within the standard well that indicates that the desired amount of amplification has been achieved.

As previously stated, the reference well maintains a level of fluorescence indicative of no amplification having occurred. Therefore, as is more fully described below, to determine the amount of amplification that has occurred within any given well, the amount of fluorescence contained within that well is compared with the amount of fluorescence in the reference well. However, due to various factors such as physical variations in the wells 4 (FIG. 11) or variations in the amount of reaction mixture contained within different wells 4 (FIG. 11), there may be some variation between the reference well fluorescence and the initial fluorescence in the remaining wells. Consequently, the percentage change of fluorescence within a given reaction well cannot be accurately determined solely through a comparison with the reference well. Rather, a factor should be utilized to compensate for any variation between the initial fluorescence in the reference well and that in the remaining wells. Consequently, before any amplification takes place to reduce the fluorescence in the remaining wells, a measurement of the initial fluorescence contained within each of these wells is taken.

Prior to taking a measurement of the initial fluorescence within each well, it is desirable to have the microtiter plate 2 undergo a few heating/cooling cycles. This process is desirable because some changes in fluorescence unrelated to amplification are caused by temperature cycling. For example, seals are typically provided over each of the wells 4 in the microtiter plate 2 and the transparency of these seals is altered when they are heated and cooled. Additionally, the initial heating/cooling cycles remove the effects of some chemical changes, caused by temperature cycling, which result in fluorescence change that is unrelated to amplification. Because of these effects, it is desirable to execute a few heating/cooling cycles to cause these changes prior to measuring the initial fluorescence within each of the wells.

After the microtiter plate 2 has been subjected to these initial heating/cooling cycles, the microtiter plate 2 is placed within the detection unit illustrated in FIG. 12. Thereafter, computer 22 executes a program that detects the initial level of fluorescence within each well and stores a value for each well indicating the ratio of the initial fluorescence within that well to the level of fluorescence in the reference well. The initial reading program executes each of the steps shown in the flow chart of FIG. 17. In step 100, the program calls subroutine Readwells.

Figure 18:
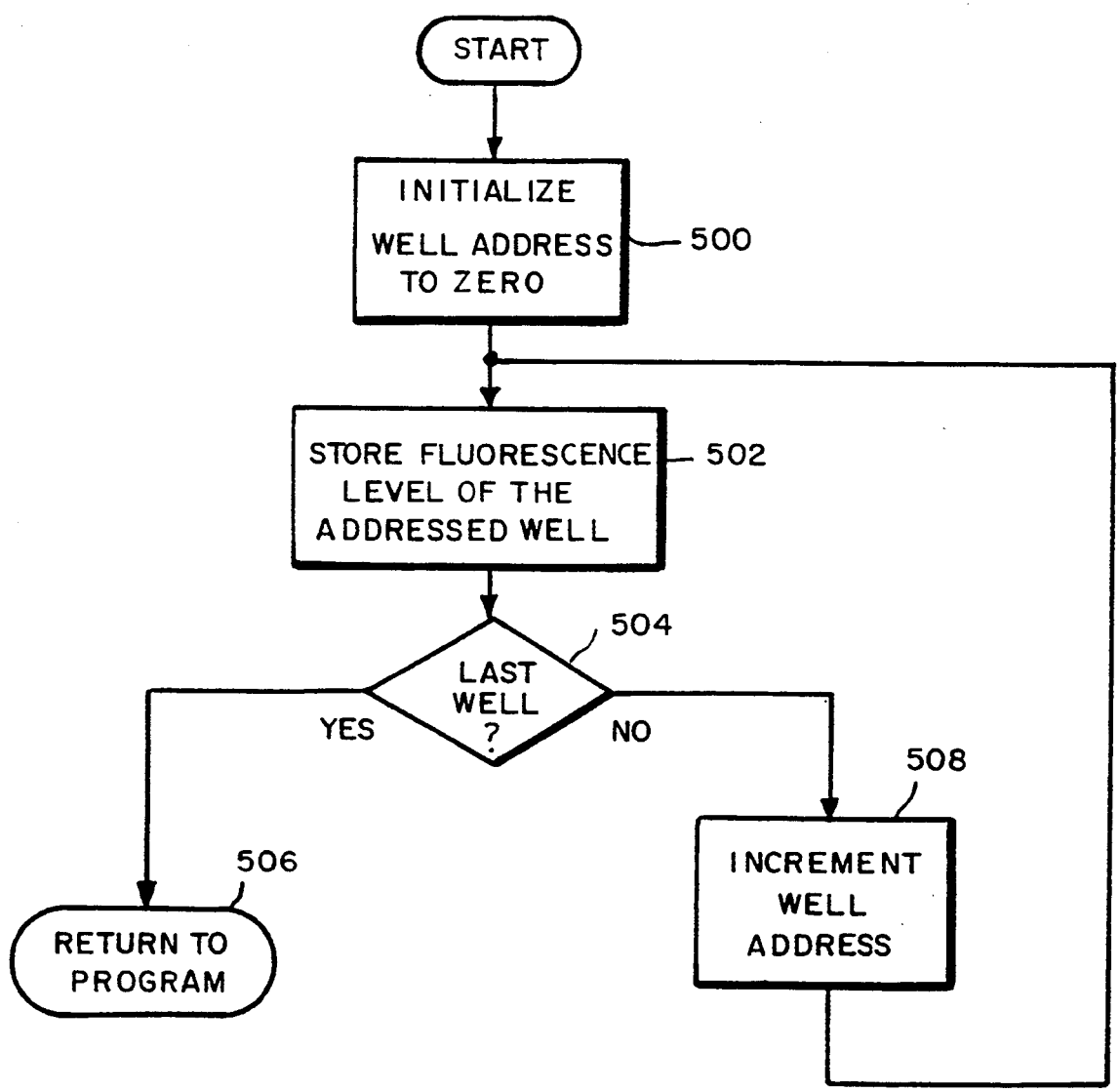
FIG. 18 is a flowchart illustrating subroutine Readwells which is a method for reading the fluorescent level of every well in the microtiter plate.

Subroutine Readwells is illustrated by a flow chart shown in FIG. 18. In step 500, the well address is initialized to zero. The well address indicates which of the wells 4 (FIG. 11) of the microtiter plate 2 is to be positioned adjacent the opening 14 of the optical cable 12. The method by which the wells 4 are addressed can be accomplished in a number of different ways. One method of addressing is to map well address zero to well A1 shown in FIG. 11. When this well is chosen as well address zero, step 100 will initialize the well address to zero by providing control signals from the computer 22 to the position control unit 20 in a manner that causes the position control unit 20 to direct the stepper motors 18 to position well A1 above the opening 14 of the optical cable 12.

In step 502, the fluorescence level emitted from the well positioned adjacent opening 14 of optical cable 12 is stored in computer 22. As was previously explained, the light received from the addressed well is passed through optical cable 12, band pass filter 28, and optical cable 30 to photomultiplier tube 32 where it is converted into electrical signals. The electrical signals are thereafter passed through data acquisition unit 36 into computer 22 where information is stored indicating the level of fluorescence emitted from the addressed well. In step 504, a test is conducted to determine whether the addressed well is the last well on the microtiter plate 2. In this manner, it can be determined whether the fluorescence for each well in the microtiter plate 2 has already been stored in the computer 22. If the addressed well from step 502 is determined in step 504 to be the last well, subroutine Readwells, in step 506, returns to the portion of the program which called the subroutine. If step 504 determines that the address well is not the last well, the well address is incremented in step 508. Well address incrementation can be accomplished in a number of ways within the computer 22. For example, as shown in FIG. 11, the well addresses can be mapped such that an incrementation of the well address generally signifies advancement along the well's X axis by one column. In this manner, assuming that well address zero is mapped to well A1, well address one is mapped to well A2, well address two is mapped to well A3, etc. When the boundary of a well row has been reached, the incrementation of the well address can map to the well specified by column 1 of the row indicated by the subsequent alphabetical letter. For example, incrementing the well address from eleven (A12) to twelve would map address twelve to well B1. Based upon this addressing scheme, the last well address is mapped to well H12.

Once the well address has been incremented, subroutine Readwells returns to step 502 so that the fluorescence of the well addressed by the newly incremented address is stored in the computer 22. In this manner, the fluorescence level for each well 4 within the microtiter plate 2 is stored within the computer 22.

Figure 17:
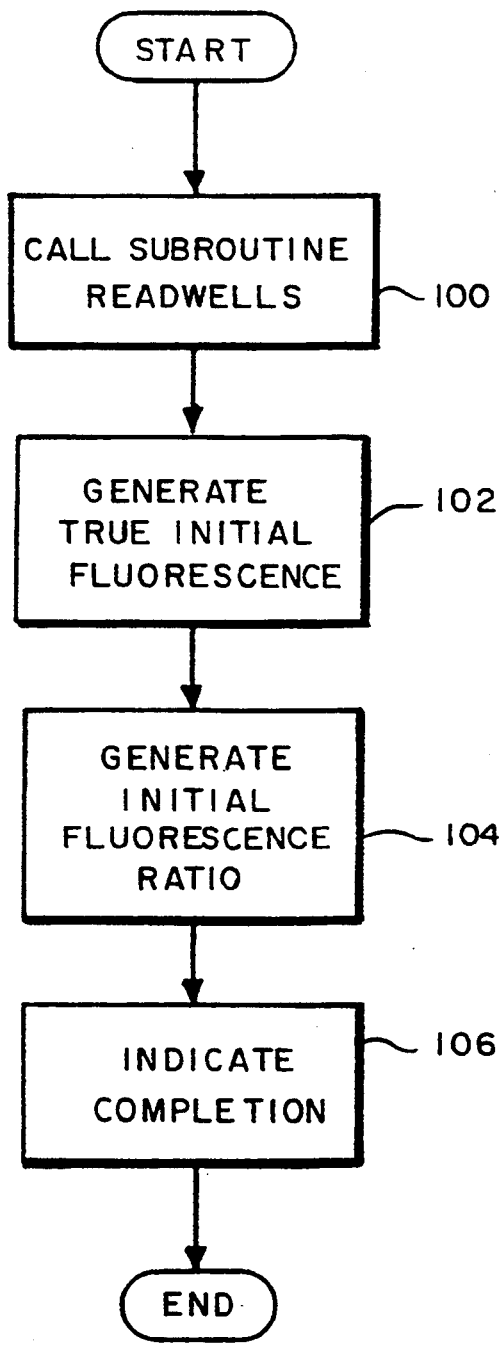
FIG. 17 is a flowchart illustrating a method of determining an initial fluorescence ratio for each well within a microtiter plate.

Once subroutine Readwells has completed, the method illustrated in FIG. 17, in step 102, generates a true initial fluorescence for each well. As used herein, the term "true fluorescence" indicates the amount of fluorescence emitted solely by the acceptor fluorophore, without the inclusion of any other sources. Step 102 could be accomplished in a number of different ways. One manner of accomplishing this step is to utilize the computer 22 to subtract the fluorescence level of the background well from the fluorescence level of each well. The result of this subtraction is the true fluorescence for each well and this true fluorescence is stored by the computer 22 for later use.

In step 104, an initial fluorescence ratio is determined for each well 4 within the microtiter plate 2. For any given well, the initial fluorescence ratio is generated by dividing its true fluorescence (determined in step 102) by the true fluorescence of the reference well. The initial fluorescence ratio for each well is then stored by the computer 22. At the completion of step 104, the method indicates in step 106 that the method has completed. Step 106 can be accomplished in a number of ways including the use of a terminal (not shown) or printer (not shown) connected to the computer 22 which could provide an indication that the method has completed.

Figure 19:
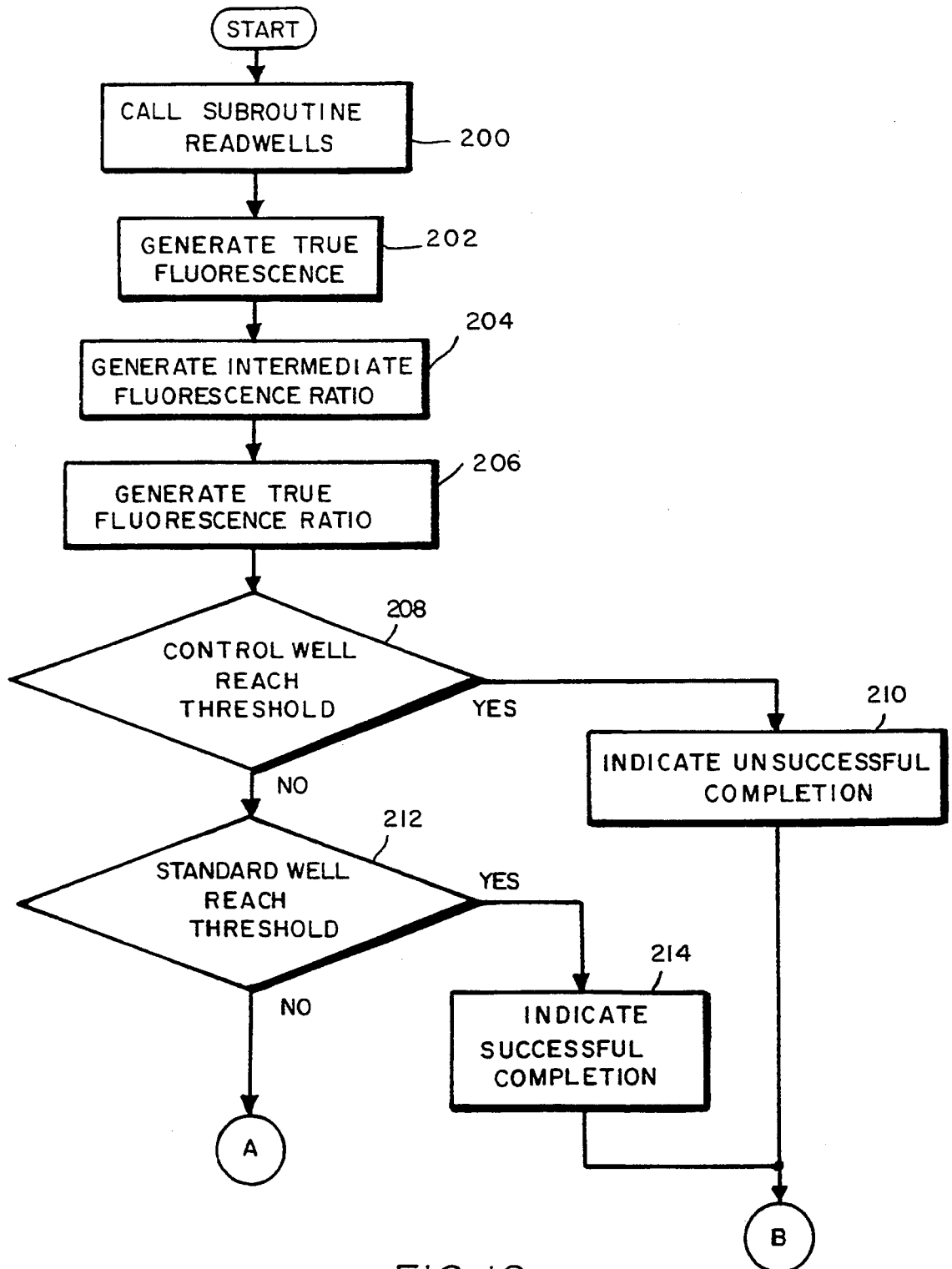
FIG. 19 is a flowchart illustrating the beginning steps of the detection method of the present invention.

Once the initial reading method has completed, the microtiter plate 2 is manually removed from the detection system illustrated in FIG. 12 and is placed into a heating/cooling apparatus (not shown) to undergo a selected number of heating/cooling cycles intended to achieve a desired level of amplification. Once the desired number of heating/cooling cycles has been executed, the microtiter plate 2 is removed from the heating/cooling apparatus and is returned to the detector system illustrated in FIG. 12. Thereafter, a detection program, illustrated in FIG. 19 is executed to detect the level of amplification that has been achieved within each well 4 of the microtiter plate 2 and to provide an indication of whether the amplification process should be terminated.

In step 200, the detection program calls subroutine Readwells (FIG. 18). As a result of the execution of subroutine Readwells, the level of fluorescence for each well within the microtiter plate 2 is stored in the computer 22. In step 202, the true fluorescence for each of the wells is determined. The generation of the true fluorescence is accomplished in the same manner as was described in step 102 for the generation of the true initial fluorescence. In step 202, the level of fluorescence for the background well is subtracted from the level of fluorescence for each of the remaining wells to generate a true fluorescence for each well. The true fluorescence for each well is thereafter stored within the computer 22.

In step 204, an intermediate fluorescence ratio is generated for each well. The intermediate fluorescence ratio is generated by dividing the true fluorescence of each well by the true fluorescence of the reference well. Thereafter, the intermediate fluorescence ratio for each well is stored within the computer 22.

In step 206, a true fluorescence ratio is generated for each well. The true fluorescence ratio is generated by dividing the intermediate fluorescence ratio for each well by the corresponding initial fluorescence ratio that was stored for that well in step 104. As previously stated, the intermediate fluorescence ratio is divided by the corresponding initial fluorescence ratio in this manner to account for any differences between the initial fluorescence of a given well and the initial reference well fluorescence. As a result, the true fluorescence ratio generated by step 206 for each well indicates the percentage change in fluorescence which has occurred for that well.

Rather than generating the true fluorescence ratio in the manner described above, an alternate method could be utilized that would derive similar information in a somewhat different manner. During step 102, an initial fluorescence was stored for each well. Therefore, this initial fluorescence could be directly compared with the true fluorescence generated in step 202 to generate a value that is similar to the true fluorescence ratio generated in step 206 for each well. If this method were utilized, no reference well would be required. However, it is preferable to utilize the reference well in the manner illustrated in FIG. 19 because it allows the percentage change in fluorescence due to amplification to be detected more accurately. Various outside factors can cause a change in fluorescence that is not due to amplification. These outside factors can include temperature variations, light variations and the like. These outside factors will cause a uniform change in fluorescence among every well 4 (FIG. 11) within the microtiter plate 2. By comparing the fluorescence level within each well with the reference well, these changes are cancelled out and, therefore, the change in fluorescence due to these factors is not erroneously interpreted as having occurred due to amplification.

In step 208, a check is conducted to determine whether the true fluorescence ratio of the control well, as generated in step 206, has reached the control well threshold level that was stored within the computer 22 prior to beginning execution of the detection program. If the true fluorescence ratio of the control well reaches this threshold level, it indicates that the desired level of amplification will not be able to take place in the reaction wells and that the reaction process should be halted. Therefore, if it is determined in step 208 that the control well threshold level has been reached, the method, in step 210, indicates that the amplification process should be terminated because it has been unsuccessful. The indication in step 210 can be accomplished in a number of ways. For example, a terminal or printer connected to the computer 22 could be utilized to perform this step.

If the control well threshold level has not been reached, the method proceeds to step 212 where a determination is made as to whether the standard well threshold level has been reached. As was previously described, prior to beginning execution of the detection program, a standard well threshold level is stored within the computer 22. This standard well threshold level indicates that the desired amount of amplification has been achieved and that the amplification process should therefore be halted. The determination in step 212 is made by comparing the true fluorescence ratio of the standard well with the standard well threshold level that is stored in the computer 22. This comparison can be accomplished in a number of ways by the computer 22. If it is determined in step 212 that the standard well threshold level has been reached, the method, in step 214, indicates that the amplification process has been successfully completed. Once again, this indication process can be accomplished in a number of ways, including through the use of a terminal or printer connected to the computer 22.

After completing either step 210 to indicate successful completion or step 214 to indicate unsuccessful completion, the method, in step 218 (FIG. 20), outputs the true fluorescence ratios for each of the wells 4 (FIG. 11) within the microtiter plate 2. As was previously stated, the true fluorescence ratios are stored within the computer 22 in step 206. Therefore, the outputting of these ratios in step 216 can be accomplished in a number of ways, including through the use of a terminal or printer attached to the computer 22. In this manner, the true fluorescence ratio for each well 4 (FIG. 11) within the microtiter plate 2 can be examined by an operator.

Figure 20:
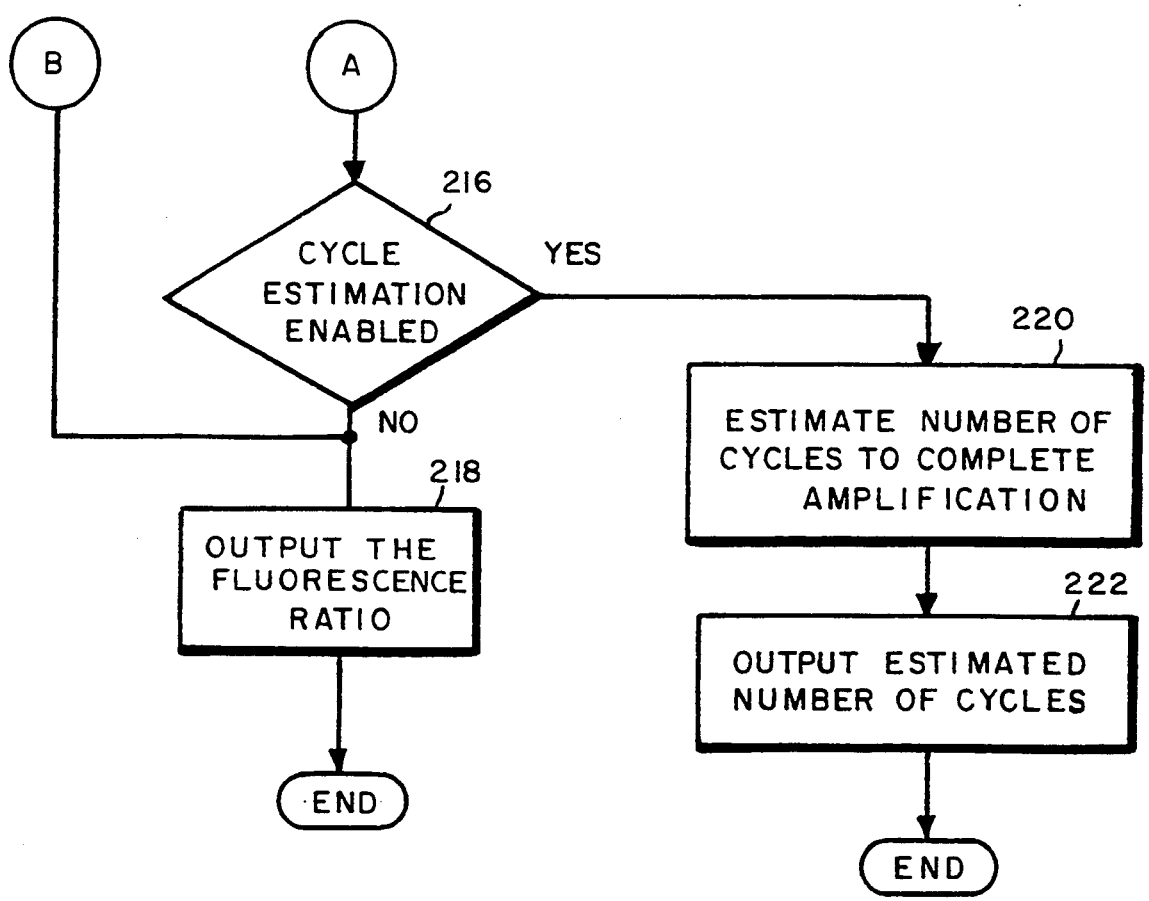
FIG. 20 is a flowchart that is a continuation of the flowchart illustrated in FIG. 19 and illustrates the remaining steps of the detection method of the present invention.

If it is determined in step 212 that the standard well threshold level has not been reached, the method proceeds to step 216 (FIG. 20). Advancement of the detection program to step 216 indicates that the amplification process has not yet been completed. Therefore, the microtiter plate 2 must be physically removed from the detection unit illustrated in FIG. 12 and transported to the heating/cooling unit (not shown) where an additional number of heating/cooling cycles are executed. In step 216, the detection program determines whether cycle estimation has been enabled. As was previously described, prior to beginning execution of the detection program, information is stored within the computer 22 indicating whether or not cycle estimation is to be enabled. When the detection program determines in step 216 that cycle estimation is not enabled, the method will, in step 218, output the true fluorescence ratios for each of the wells within the microtiter plate 2 as the last step of the method. The outputting of the true fluorescence ratios can be accomplished in a number of ways, including through the use of a terminal or printer connected to the computer 22. An operator can examine this information and make a determination as to how many additional heating/cooling cycles need to be executed to complete the amplification process.

If the method determines in step 216 that cycle estimation is enabled, the method, in step 220, estimates the number of heating/cooling cycles that will be necessary to complete the amplification process. The estimation in step 220 can be accomplished in a number of ways. One way of performing the estimation is by storing a look-up table within the computer 22 prior to beginning execution of the detection program. Through experimentation, the look-up table can be developed to establish an estimated number of heating/cooling cycles that will be required to advance the amplification process from given stages to completion. The stage of the amplification process is determined by examining the true fluorescence ratio of the standard well. Therefore, the true fluorescence ratio of the standard well, as determined in step 206, can be utilized to address the look-up table which will thereafter output an estimated number of heating/cooling cycles necessary to complete the amplification process. Once this estimated number of cycles is determined, the method, in step 222, outputs the estimated number of cycles. The outputting of the estimated number of cycles in step 222 can be accomplished in a number of ways including through the use of a terminal or printer connected to the computer 22. An operator thereafter utilizes the estimated number of cycles to program the heating/cooling apparatus to execute the number of cycles necessary to complete the amplification process.

Amplification/Detection Method

A description is now provided of the manner in which computer 22 is programmed to control the apparatus illustrated in FIG. 15 to implement an amplification/detection method for generating amplification and automatically detecting the amount of amplification that has occurred within each of the wells of microtiter plate 2. As was previously described, the apparatus illustrated in FIG. 15 is a self-contained apparatus for executing heating/cooling cycles to stimulate amplification, and for detecting the level of amplification that has been achieved. Consequently, the amplification/detection program differs from the detection program described above because it performs the heating/cooling steps which stimulate amplification, as well as the steps involved in detecting the level of amplification that has been achieved.

Before beginning the execution of the amplification/detection program on computer 22, a series of initialization steps are conducted to determine certain testing parameters and to initialize the system. First, addresses are provided for the reference, standard, control and background wells. The wells serve the same purpose as was described in relation to the detection program utilizing the apparatus of FIG. 12. Second, threshold levels for the control and standard wells are stored. These threshold levels also serve the same purpose as the threshold levels described in connection with the detection program utilizing the apparatus illustrated in FIG. 12. Third, a number of initialization heating/cooling cycles defining an initial counter threshold is stored. The initial counter threshold indicates a number of heating/cooling cycles to be run on the microtiter plate 2 prior to determining the initial fluorescence ratio of each well. As was previously described in connection with the detection program, it is desirable to execute a few heating/cooling cycles prior to determining the initial fluorescence of each well because these cycles may possibly cause a change in the fluorescence of the wells due to temperature cycling. Fourth, the duration and temperature of each heating/cooling cycle is indicated. This information allows the computer 22 to issue commands to the temperature control unit 38 and thereby control the heating and cooling conditions applied to the microtiter plate 2. Fifth, the number of heating/cooling cycles that is to be executed between detection sampling is indicated. This information is utilized to determine when to perform the detection portion of the amplification/detection program. Sixth, information indicating whether the estimation function is enabled. This information is utilized by the amplification/detection program to control the determination of the number of heating/cooling cycles to be executed following a detection that the amplification process has not yet been completed. If the estimation function is enabled, information is also stored in the computer 22 to provide a basis for estimating the number of cycles needed to complete the amplification process. As was described in connection with step 216 of the detection program, one way of providing this estimation information is to provide a look-up table that provides an estimated cycle number based upon various values of the standard well's true fluorescence ratio. Seventh, a cycle counter is established and initialized. The cycle counter can be implemented in many ways, including the use of a storage element within the computer 22 that is capable of being incremented.

Figure 21:
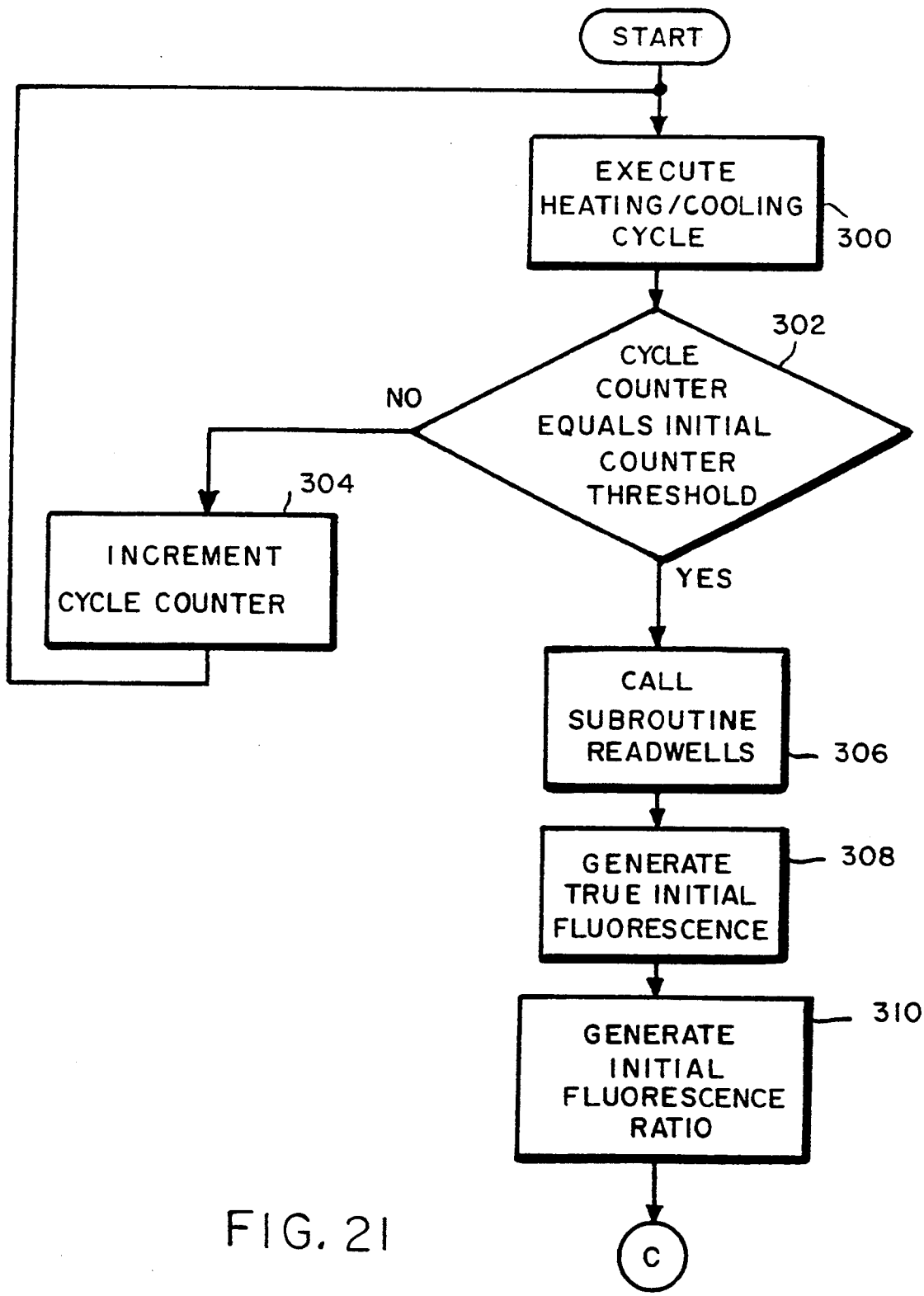
FIG. 21 is a flowchart illustrating the beginning steps of the amplification/detection method of the present invention.

FIG. 21 is a flowchart that describes the amplification/detection program carried out by the apparatus illustrated in FIG. 15. In step 300, the method executes a heating/cooling cycle. This step is accomplished by the computer 22 issuing control signals to the temperature control unit 38 which responds by executing one heating/cooling cycle.

Step 302 determines whether the cycle counter equals the initial counter threshold that was stored in the computer 22 prior to beginning execution of the method. If it is determined in step 302 that the cycle counter does not equal the initial counter threshold, the method, in step 304, increments the cycle counter. Step 304 can be accomplished in a number of ways including the use of a storage element within the computer 22 which is capable of being incremented. Once the cycle counter is incremented in step 304, the method returns to step 300 and executes another heating/cooling cycle. In this manner, a number of heating/cooling cycles are executed until it is detected in step 302 that the cycle counter equals the initial counter threshold.

Once it is determined in step 302 that the cycle counter equals the initial counter threshold, the method, in step 306, calls subroutine Readwells (FIG. 18). As was previously explained, subroutine Readwells examines every well within the microtiter plate 2 and stores the initial fluorescence level of each of these wells within the computer 22.

In step 308, the method generates a true initial fluorescence for every well within the microtiter plate 2. This step is analogous to step 102 that was previously described in connection with the method illustrated in FIG. 17. In step 308, the background well fluorescence is subtracted from the fluorescence of each of the remaining wells to provide a true indication of the fluorescence within those wells. Thereafter, in step 310, the method generates an initial fluorescence ratio. This step is analogous to step 104 that was described in connection with the method illustrated in FIG. 17. The initial fluorescence ratio is determined by dividing the true fluorescence of a given well by the true fluorescence of the reference well. The initial fluorescence value for each well is stored in the computer 22.

In step 312 (illustrated in FIG. 22), the method resets the cycle counter. The cycle counter is reset during step 312 to enable the cycle counter to be utilized to determine the number of heating/cooling cycles that will subsequently be executed. In step 314, the method executes a heating/cooling cycle. Step 314 is accomplished by providing control signals from the computer 22 to the temperature control unit 38. The duration and temperature of the heating/cooling cycle is determined by the initial information that was stored within the computer 22 prior to beginning execution of the amplification/detection program.

In step 316, a determination is made as to whether the cycle counter equals the number of cycles that is to be executed between detection sampling. Step 316 is accomplished by comparing the cycle counter with the number of cycles to be executed between detection sampling which was stored within the computer 22 prior to beginning execution of the amplification/detection program. If it is determined in step 316 that the cycle counter does not equal the number of cycles between detection sampling, the method increments the cycle counter in step 318. Thereafter, the method returns to step 314 and executes another heating/cooling cycle. In this manner, a number of heating/cooling cycles is executed until it is determined in step 316 that the cycle counter equals the number of cycles between detection sampling. Once that determination is made, the method, in step 320, calls subroutine Readwells (FIG. 18). As a result of the execution of subroutine Readwells, a fluorescent level is stored for each well within the microtiter plate 2.

Figure 23:
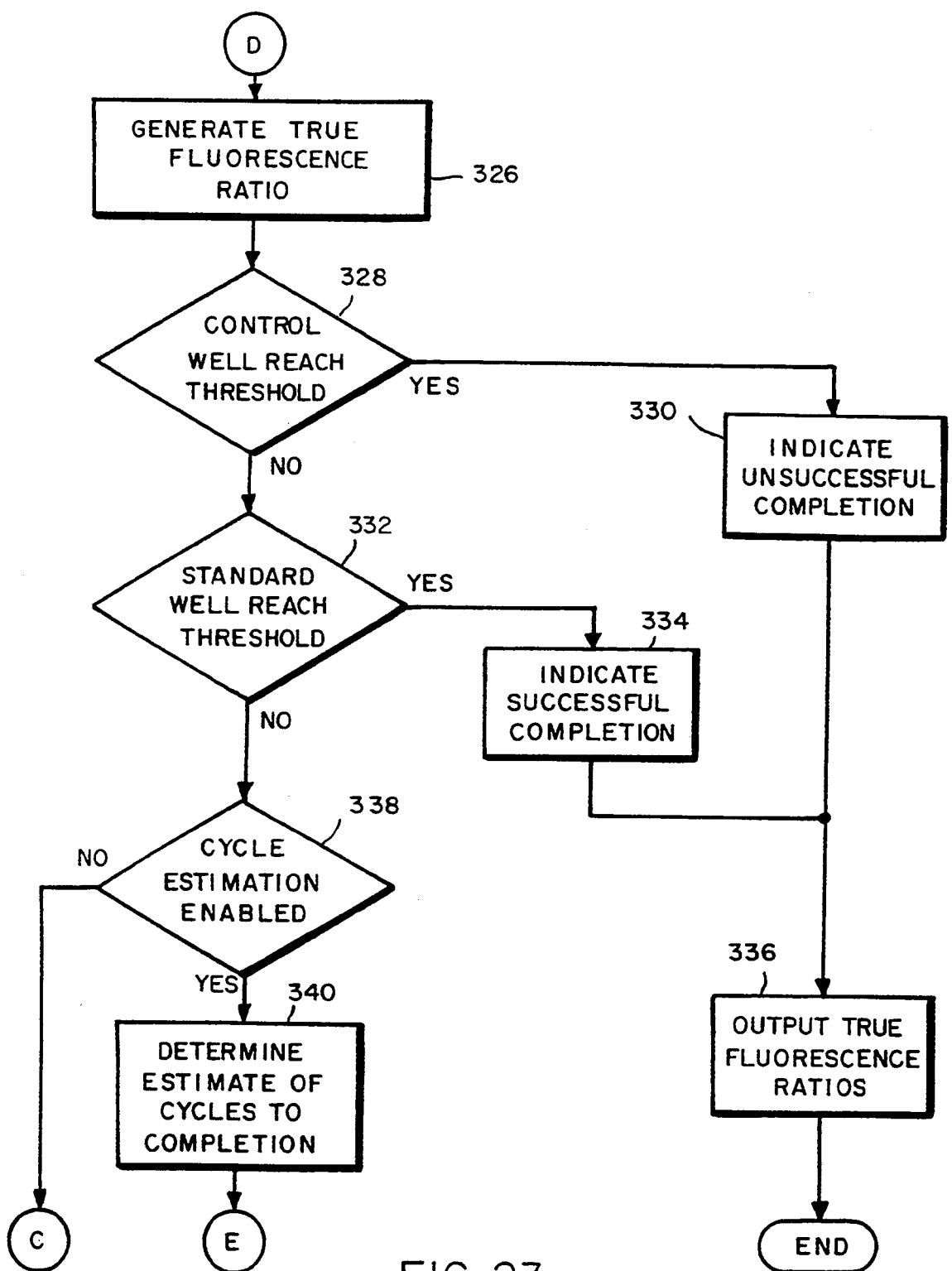
FIG. 23 is a flowchart that is a continuation of the flowchart in FIG. 22 and illustrates additional steps of the amplification/detection method of the present invention.

Thereafter, in step 322, the method generates a true fluorescence value for each well within the microtiter plate 2. This step is analogous to step 202 which was described in connection with the detection program illustrated in FIG. 19. The true fluorescence for each well is generated in step 322 by subtracting the fluorescence level of the background well from the fluorescence level of each remaining well. In step 324, the method generates an intermediate fluorescence ratio for each well within the microtiter plate 2. This step is analogous to step 204 which was described in connection with the method illustrated in FIG. 19. The intermediate fluorescence ratio is generated in step 324 by dividing the true fluorescence of each well by the true fluorescence of the reference well. In step 326 (illustrated in FIG. 23), the method generates a true fluorescence ratio for each well within the microtiter plate 2. This step is analogous to step 206 that was described in connection with the flow chart illustrated in FIG. 19. The true fluorescence ratio is generated in step 326 by multiplying the intermediate fluorescence ratio for each well by the initial fluorescence ratio generated for that well in step 310.

In step 328, a determination is made as to whether the control well fluorescence has reached the control well threshold. This determination is analogous to the determination that was made in step 208 described in connection with the method illustrated in FIG. 19. The determination in step 328 is made by comparing the true fluorescence value of the control well with the control well threshold that was stored in the computer 22 prior to beginning execution of the amplification/detection program. As was previously described in connection with step 208, a determination that the control well fluorescence has reached the threshold indicates that the desired amount of amplification will not be able to take place satisfactorily within the reaction wells and that the reaction process should therefore be terminated. Consequently, when it is determined in step 328 that the control well fluorescence has reached the threshold, the method completes two final steps, i.e. steps 330 and 336, and then terminates. In step 330, the method indicates that the amplification process should be terminated because it has been unsuccessful. Step 330 is analogous to step 210 that was described in connection with the method illustrated in FIG. 19 and can be accomplished in a number of ways, including through the use of a terminal or printer connected to the computer 22 to provide an indication that the test should be terminated because it has been unsuccessful. In step 336, the method outputs the true fluorescence ratios for each of the wells within the microtiter plate 2. Step 336 is analogous to step 218 that was previously described in connection with the method illustrated in FIG. 20. Step 336 can be accomplished in a number of ways, including through the use of a terminal or printer connected to the computer 22. The outputting of the true fluorescence ratios for each well within the microtiter plate 2 allows an operator to examine this information which indicates the extent of amplification that has occurred within each well. By terminating in this manner, the method does not return to step 314 and therefore does not execute any further heating/cooling cycles on the microtiter plate 2.

If a determination is made in step 328 that the control well has not reached its threshold, the method proceeds to step 332 where a determination is made as to whether the standard well fluorescence has reached its threshold. Step 322 is analogous to step 212 that was described in connection with the method illustrated in FIG. 19. Step 332 is accomplished by comparing the true fluorescence ratio of the standard well with the standard well threshold that was stored within the computer 22 prior to beginning execution of the amplification/detection program. As was explained previously in connection with step 212, a detection that the standard well has reached its threshold indicates that the desired amount of amplification has been achieved and that no more heating/cooling cycles need be executed. Therefore, when it is determined in step 332 that the standard well has reached its threshold, the method completes two final steps, i.e. steps 334 and 336, and then terminates. In step 334, the method indicates that the amplification process has been successfully completed. Step 334 is analogous to step 214 that was described in connection with the method illustrated in FIG. 19. Step 334 can be conducted in a number of ways, including through the use of a terminal or printer connected to the computer 22 for providing information indicating that the step has been successfully completed. In step 336, the method outputs the true fluorescence ratios for each of the wells within the microtiter plate 2. As was previously stated, step 336 can be accomplished in a number of manners including through the use of a terminal or printer connected to the computer 22. The outputting of the true fluorescence ratios for each well within the microtiter plate 2 allows an operator to examine this information which indicates the extent of amplification that has occurred within each well. By terminating in this manner, the method does not return to step 314 and therefore does not execute any further heating/cooling cycles on the microtiter plate 2.

Figure 22:
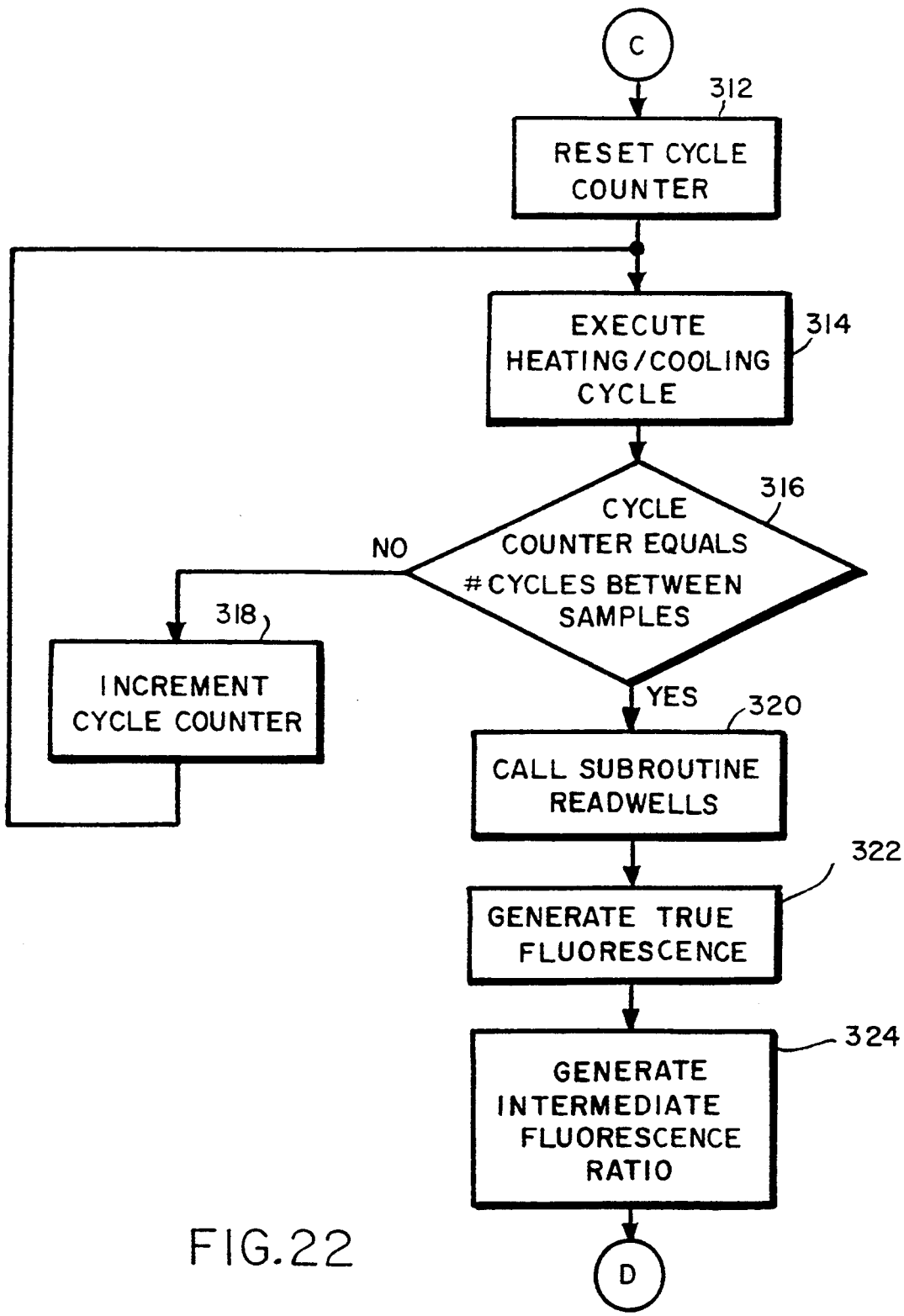
FIG. 22 is a flowchart that is a continuation of FIG. 21 and illustrates further steps of the amplification/detection method of the present invention.

If it is determined in step 332 that the standard well has not reached its threshold, then additional heating/cooling cycles need to be executed. In step 338, the method determines whether cycle estimation is enabled. Step 338 is performed by determining whether the information stored within the computer 22 prior to beginning execution of the amplification/detection program indicates that cycle estimation is to be enabled. If it is to be determined in step 338 that cycle estimation is not enabled, then the method returns to step 312 (FIG. 22). In this manner, the method will re-execute steps 312, 314, 316 and 318 to perform a number of heating cycles that is equal to the number of cycles to be executed between detection samplings which was stored in the computer 22 prior to beginning execution of the amplification/detection program. As a result, the cycle estimation feature is not utilized. However, if it is determined in step 338 that cycle estimation is enabled, the method, in step 340, determines an estimate of the number of heating/cooling cycles that need to be executed to complete the amplification process. Step 340 can be accomplished in a number of ways. For example, the estimate of the number of cycles necessary to complete the amplification process can be provided by examining the true fluorescence ratio of the standard well and applying it to the look-up table that was stored within the computer 22 prior to beginning execution of the amplification/detection program. Based upon this true fluorescence ratio of the standard well, the look-up table provides an estimated number of heating/cooling cycles necessary to complete the amplification process.

Figure 24:
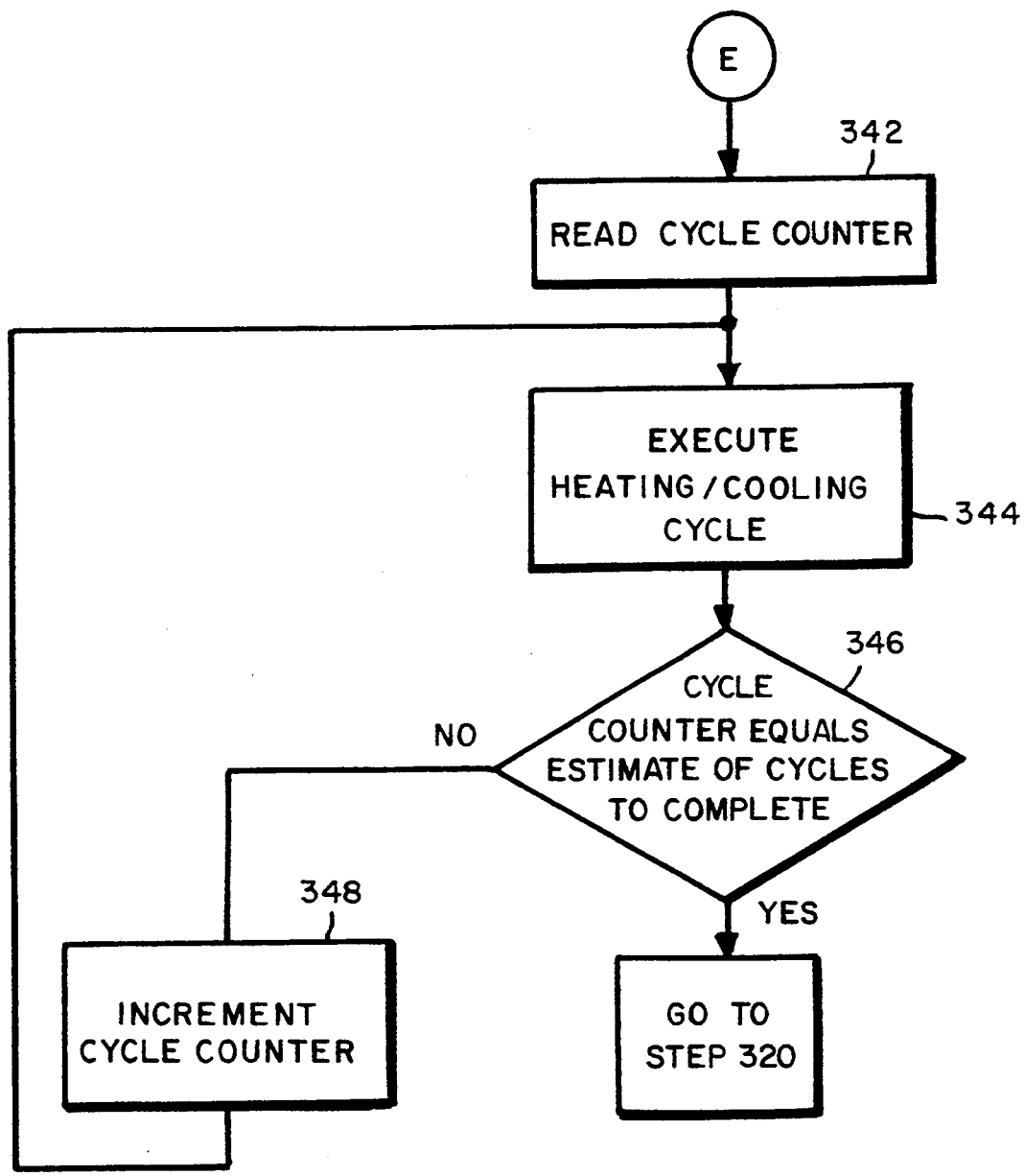
FIG. 24 is a flowchart that is a continuation of the flowchart in FIG. 23 and illustrates the remaining steps of the amplification/detection method of the present invention.

Once an estimated number of cycles is determined in step 340, the method resets the cycle counter in step 342 (FIG. 24). Thereafter, in step 344, the method executes a heating/cooling cycle. Following the execution of the heating/cooling cycle, the method determines, in step 346, whether the cycle counter equals the estimated number of cycles to be executed. If the method determines in step 346 that the cycle counter does not equal the estimated number of cycles to completion, it increments the cycle counter in step 348. Thereafter, the method returns to step 344 wherein an additional heating/cooling cycle is executed. In this manner, a number of heating/cooling cycles are executed until it is determined in step 346 that this number, as indicated by the value of the cycle counter, equals the estimated number of cycles required to complete the amplification process. When it is determined in step 346 that the cycle counter equals the estimated number required for completion, the method returns to step 320 (FIG. 22). By returning to step 320, the method proceeds to detect and store true fluorescence ratios for each well. Thereafter, the method determines whether the amplification process has been completed as a result of the execution of the estimated number of cycles. In this manner, the method will continue until either (1) it is detected in step 328 that the amplification method has been unsuccessfully completed, or (2) it is detected in step 332 that the amplification method has been successfully completed.

Because of the particular configurations of fluorophores chosen in the preferred embodiment of the invention, both the detection program illustrated in FIG. 19 and the amplification/detection program illustrated in FIG. 21 utilize a percentage decrease in fluorescence as an indication of the amount of amplification that has taken place. However, other configurations of fluorophores could be utilized that would generate an increase in fluorescence as amplification increased. It should be understood that the methods illustrated in FIGS. 19 and 21 could also be utilized to perform amplification detection based upon in increase in fluorescence if the selected fluorophores so require. If the fluorophores were chosen such that an increase in fluorescence indicated an increase in amplification, the reference well would be established to indicate a reference of the minimum amount of fluorescence achieved, rather than a maximum amount. However, since the methods operate by determining a percentage change in fluorescence, the methods are generic and can be utilized to detect increasing, as well as decreasing fluorescence. Therefore, no change is required to the above-described apparatuses or methods to detect amplification based upon an increase in fluorescence.

The methods and apparatus for detecting amplification through changes in fluorescence that have been described herein are preferable because they provide an automated system for taking readings of each well within the microtiter plate 2 and for processing the information to provide it in a desirable form. However, it should be understood that the present invention could be practiced through the use of other apparatus and/or apparatus that does not provide all of the automated features of the embodiments disclosed herein.

The following Examples are illustrative of the invention but should not be considered as limiting the scope of the invention. Described in Example 1 is an experiment demonstrating the existence of polymerization dependent probe displacement. Example 2 illustrates polymerization dependent probe displacement following repeated cycles of target DNA amplification. Example 3 provides an example of the transfer of energy between pairs of fluorophores attached to different oligonucleotide probes. The improved amplification method of the invention is compared to the standard PCR amplification method in Example 4. Example 5 describes a homogeneous assay for detection of an HBV Sequence in human genomic DNA.

EXAMPLE 1

Polymerization Dependent Strand-Displacement

The probes were designed such that extension probe Sequence I.D. Number 1 and lagging probe Sequence I.D. Number 2 were separated by a gap of one nucleotide when hybridized to template Sequence I.D. Number 3. This gap is illustrated in FIG. 7, wherein the "gap" nucleotide (A) on the template is underlined and appears in boldface print. Lagging probe Sequence I.D. Number 2 includes two nucleotides at its 3' end which extend beyond the 5' end of template Sequence I.D. Number 3. This nucleotide protrusion is also illustrated in FIG. 7, wherein the nucleotides (CA) are underlined and also appear in boldface print.

The experiment was designed to illustrate polymerization dependent strand displacement as a prevalent phenomenon. Ligation of extension primer Sequence I.D. Number 1 and lagging probe Sequence I.D. Number 2 was included in the experiment in order to demonstrate that hybridization of the lagging probe to the template is a prerequisite for polymerization dependent strand-displacement. In a ligation addition, the presence of product having a nucleotide sequence two nucleotides longer than the nucleic acid template was used as a marker for assessing whether or not a downstream lagging probe was annealed to the template as an extension reaction was taking place. Thus, in the presence of only two nucleotides, dATP and dTTP, the gap between the extension primer and the lagging probe was filled to provide a ligation product having a sequence length two nucleotides longer than the template. However, when only two nucleotides were present, elongation of the extension primer and concomitant displacement of the lagging probe was aborted due to nucleotide starvation. In contrast, in the presence of all four nucleotides, polymerization dependent strand-displacement resulted in target amplification, i.e., production of a product having a sequence length identical to that of the template.

Extension primer Sequence I.D. Number 1 (0.1 μg) was 5' end labelled with $^{32}$P by polynucleotide kinase. The reaction volume of 20 μl contained the buffer, consisting of 30 mM TrisHCl at pH 8.0, 90 mM NH$_4$Cl, 10 mM MgCl$_2$, 100 mM KCl, 2 mM DTT and bovine serum albumin (BSA), in addition to 10 ng of extension primer Sequence I.D. Number 1, 1 ng of the $^{32}$P labelled extension primer, 15 ng of lagging probe Sequence I.D. Number 2, 25 ng of template Sequence I.D. Number 3 and 2 nmoles of AND$^+$. For reaction mixtures non-permissive to polymerization dependent strand displacement, only 2 nmoles each of dATP and dTTP were added. For reaction mixtures permissive to the polymerization dependent strand displacement, 2 nmoles of each of the four nucleotide triphosphates were added.

The reaction mixtures were incubated at 90° C. for 3 minutes, followed by the addition of 2 units of Taq polymerase along with Tth ligase. Thereafter, the mixtures were incubated at 90° C. for 1 minute before reducing the temperature to 50° C. for 5 minutes. From each reaction mixture, a 3 μl aliquot was removed, quenched by transferring to a vessel containing 5 μl of 80% formamide and analyzed by polyacrylamide gel electrophoresis (PAGE).

Figure 2:
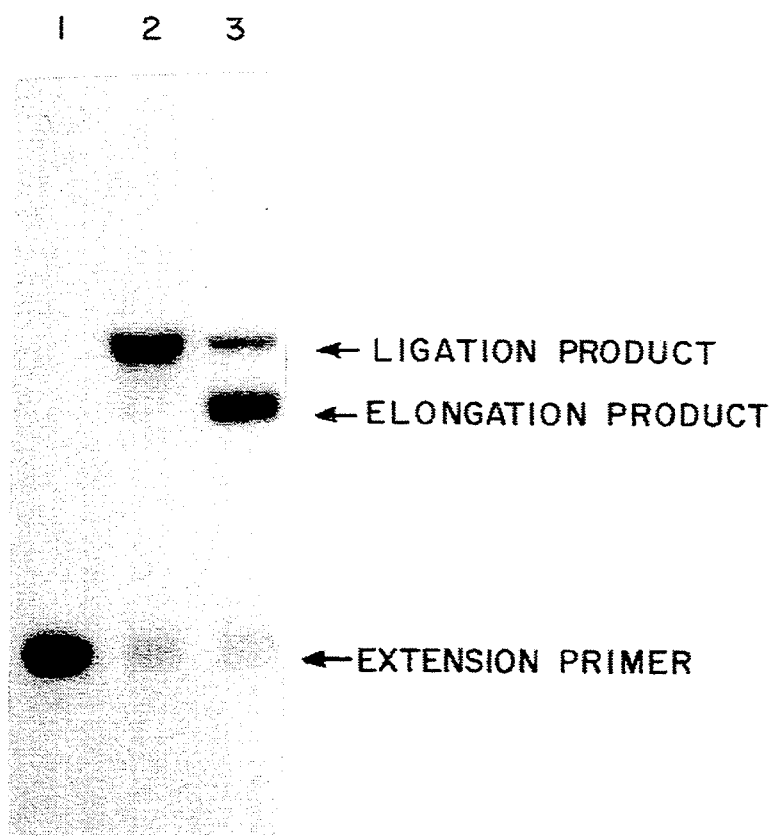
FIG. 2 shows an autoradiogram of a polyacrylamide gel electrophoresis (PAGE) gel demonstrating polymerization dependent strand-displacement as a predominant phenomenon.

The results of autoradiography of the PAGE gel are shown in FIG. 2. Lane 1 shows labelled extension primer Sequence I.D. Number 1. Lane 2 corresponds to the products of the ligation reaction, i.e., only dATP and dTTP are present. Accordingly, lane 2 shows only the initially labelled extension primer and the ligation product. Lane 3 demonstrates the effects of polymerization dependent strand-displacement when each of the four deoxynucleotides are present. Thus, when ligation and strand-displacement occurred simultaneously, strand displacement is a prevalent phenomenon, as indicated by the prominent presence in lane 3 of the elongation product, i.e., labelled amplified template, having a sequence length shorter than that of the labelled ligation product.

EXAMPLE 2

Polymerization Dependent Strand Displacement during Amplification

This experiment illustrates polymerization dependent strand displacement during repeated cycles of target DNA amplification. Two sets of duplexes, each duplex comprising one extension primer and one energy sink oligonucleotide were used. Duplex A comprises extension primer A1 and lagging probe A2. Duplex B comprises extension primer B1 and lagging probe B2. The 3' terminal hydroxy groups of each lagging probe were modified to prevent use of the probes as primers of an extension reaction.

The 5' end of extension primer A1 (a 27 mer oligodeoxyribonucleotide) and the 5' end of lagging probe B2 (a 20 mer oligodeoxyribonucleotide) were labelled with $^{32}$P. The labelled extension primer was used to monitor the products of amplification. The labelled lagging probe was used to monitor the products of strand displacement. In addition, extension primer B1 was conjugated at the amino-modified thymidine base with the fluorophore Texas Red and lagging probe A2 was conjugated at the 3' end with the fluorophore fluorescein. When the probes were hybridized to the human genomic DNA template, a one nucleotide gap was present between the 3' end of extension primer A1 and the 5' end of lagging probe B2.

For polymerase dependent strand displacement, the reactions were performed in the wells of a 96-well microtiter plate. Each reaction mixture of 20 ul total volume contained 50 mM TrisHCl pH=8.7, 10 mM NH4Cl, 80 mM KCl, 2 mM DTT, 5 mM MgCl2, 100 uM each deoxynucleotide triphosphate ("dXTP"), 0.1% of Triton-X100, 2 unit of Stoffel fragment of Taq DNA polymerase (Cetus-Perkin Elmer, Norwalk, Conn. 06859] and 30 ng of each extension primer or lagging probe. Calf thymus DNA (100 ng) was added as template to the control reaction mixtures. About $10^4$ molecules of human genomic DNA was added as template to the sample reaction mixtures. A further "Blank" control was contained 100 ng of calf thymus DNA as template but without enzyme present. $^{32}$[P]-labelled extension primer and/or labelled lagging probe (0.5 ng/each) were added to the reaction mixture. The amplification reactions were allowed to proceed for 30 cycles, each cycle consisting of 94° C. for 0.4 minute, 63° C. for 0.4 minute, and 72° C. for 0.5 minute. Thereafter, an aliquot of the reaction mixture was analyzed by application onto a 20% native polyacrylamide gel followed by autoradiography.

Figure 3:
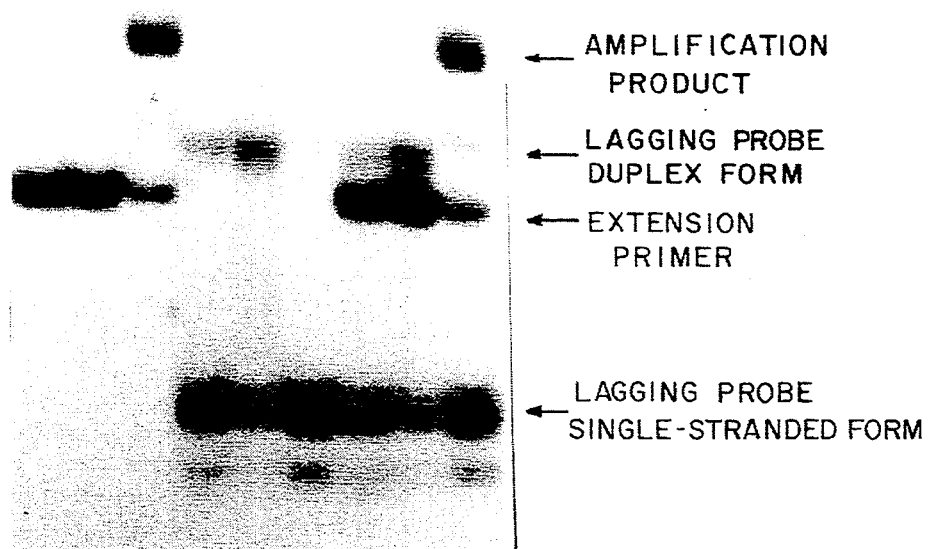
FIG. 3 shows an autoradiogram of native PAGE gel illustrating polymerization dependent strand displacement during amplification.

The results are shown in FIG. 3. A native polyacrylamide gel was used to analyze the reaction products in order to visualize extension primer:lagging probe duplexes. The identification of each lane is as follows:

1. With labelled extension primer of Duplex A as tracer, blank;
2. With labelled extension primer of Duplex A as tracer, control;
3. With labelled extension primer of Duplex A as tracer, sample;
4. With labelled lagging probe of Duplex B as tracer, blank;
5. With labelled lagging probe of Duplex B as tracer, control;
6. With labelled lagging probe of Duplex B as tracer, sample;
7. With both labelled probes as tracer, blank;
8. With both labelled probes as tracer, control;
9. With both labelled probes as tracer, sample.

With labelled extension primer as the tracer, lane 3 shows the presence of the specific amplification product and unreacted labelled extension primer. The presence of a specific amplification product is absent from lane 2, illustrating the absence of non-specific priming events in the absence of the specific template (human genomic DNA). With labelled lagging probe as the tracer, unreacted lagging probe was present in both single stranded and duplex forms (lane 4 with omission of DNA polymerase and lane 5 with omission of specific template). In contrast, specific amplification exhausted the available supply of labelled lagging probe in its duplex form, resulting in the presence of lagging probe in a single stranded form only (lane 6 in the presence of $10^4$ molecules of human genomic DNA). This example illustrates the concomitant specific amplification of target sequence and probe displacement. By using the Stoffel fragment of Taq DNA polymerase, which lacks a exonuclease activity, as the polymerization agent, the possibility of strand displacement resulting from polymerization dependent exonuclease activity was excluded.

EXAMPLE 3:

Energy Transfer for Fluorophore Conjugated Probe Pairs

This experiment illustrates the efficiency of energy transfer in duplexes containing probes having conjugated fluorophore. Either of two fluorophores, fluorescein (F) and Texas Red ($T_r$), were covalently attached to the amino modified thymidine nucleotides of extension primer Sequence I.D. Numbers 4 and 6 and lagging probe Sequence I.D. Numbers 5 and 7 (FIG. 8).

For measurement of relative fluorescent intensity, the excitation wavelength was fixed at 495 nm and the emission wavelength was at 630 nm. In a 20 ul volume containing the buffer of 50 mM TrisHCl pH=8.3, 40 ng of each probe was added and incubated at 60° C. for 3 minutes. In the absence of energy transfer, emission from both fluorescein and Texas red are minimal. The efficiency of the energy transfer is calculated according to the following formula:

$$[(\text{Probe } T_r \text{ and Probe F})\text{-Basal}] \div [(\text{Probe } T_r\text{-Basal}) + (\text{Probe F-Basal})]$$

where Probe $T_r$ is the fluorescence intensity of probe conjugated with Texas red;
Probe F is the fluorescence intensity of probe conjugated with fluorescein; and
Basal is the background fluorescence intensity.

The result is shown in Table I, in which all values are presented as the relative fluorescent intensity except for the efficiency column.

TABLE I

|  | Basal | Probe Tr | Probe F | Probe Tr and Probe F | Efficiency |
|---|---|---|---|---|---|
| Probe Pair 1 | 442 | 1412 | 1354 | 7071 | 3.52 |
| Probe Pair 2 | 512 | 1250 | 1966 | 8550 | 3.67 |

As illustrated above, the difference in energy transfer is significant for probes hybridized to one another in duplex form compared to probes which are hybridized to the template. This difference in energy transfer provides ample room for the analysis of diminishing energy transfer caused by displacement of lagging probe from the template.

EXAMPLE 4

Suppressing Non-specific Amplification in Strand Displacement Dependent Amplification This example compares the specificity of amplification for the present invention to that of a standard PCR amplification protocol (U.S. Pat. No. 4,684,195).

The probe configurations and reaction conditions are as described in Example 2. For the standard PCR reaction, only two extension primers were included in reaction mixture, i.e., no energy sink oligonucleotides were present. Extension primer B1 was labelled with $^{32}$P at its 5' end. Lagging probe A2 was labelled at the 5' end with $^{32}$P and lagging probe B2 was labelled at the 3' end with $^{32}$P. Note that in this experiment, the lagging probes are complementary to the extension primers. Thus, the lagging probes also function as energy sink oligonucleotides in greatly reducing non-specific priming events.

Either Stoffel fragment (2 U/reaction) or Taq DNA polymerase (0.3 U/reaction) was used as the polymerization agent. In one group of PCR reactions, neither extension primer was conjugated to a fluorophore. Following 30 cycles of the standard PCR reaction, an aliquot of reaction mixture was removed and analyzed by application onto a 15% 8M urea-polyacrylamide gel followed by autoradiography.

Figure 4A:
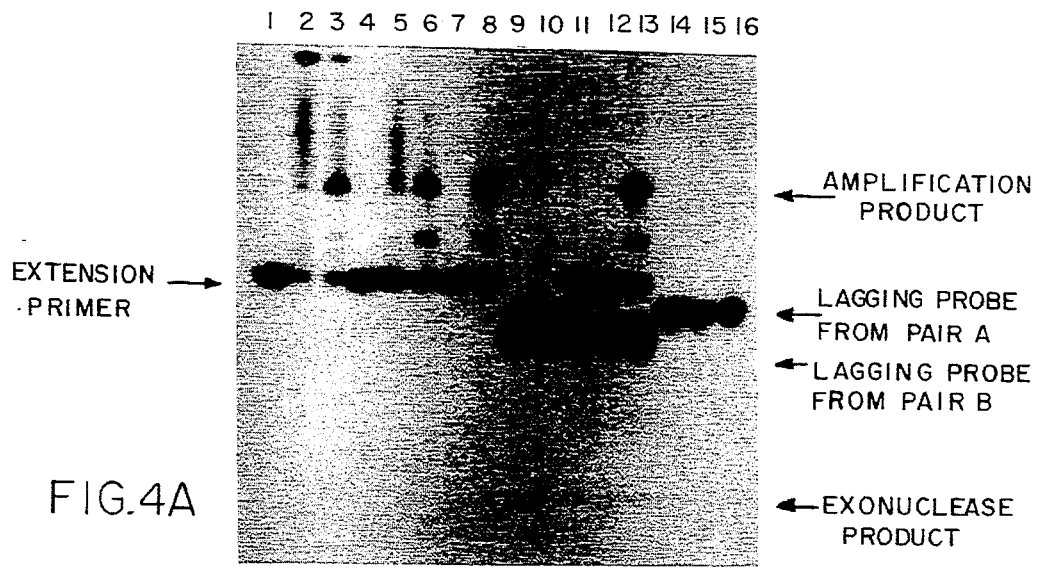
FIG. 4A and FIG. 4B show an autoradiogram of a Urea-PAGE gel illustrating distinct specificity for strand-displacement dependent amplification in comparison to PCR method, using different polymerization agents.
Figure 4B:
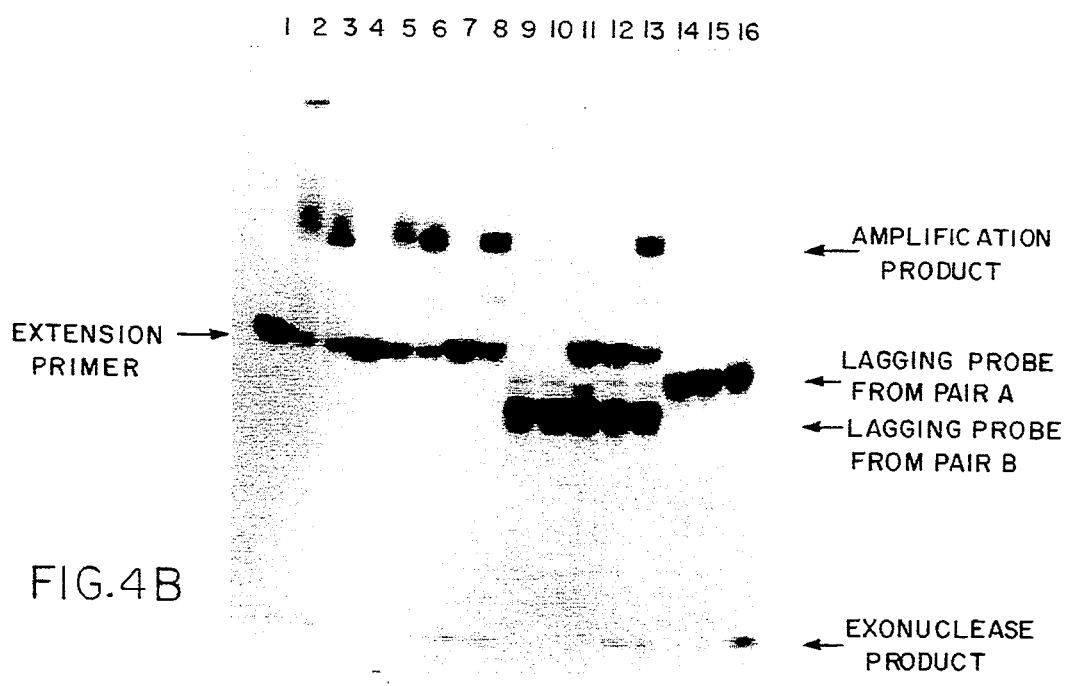

The results are shown in FIG. 4a and b. FIG. 4a shows the results of amplification reactions performed using the Stoffel fragment; FIG. 4b shows the results from amplification reactions performed using the Taq DNA polymerase. The arrangement of lanes is identical for FIG. 4a and 4b. The identification of each lane is as follows:

1. PCR assay with labelled extension primer A1 as tracer, neither extension primer labelled with fluorophore, blank;
2. Same as lane 1, control;
3. Same as lane 1, sample;
4. Same as lane 1, except that one of the extension primers was conjugated with Texas Red;
5. Same as lane 2, except that one of the extension primers was conjugated with Texas Red;
6. Same as lane 3, except that one of the extension primers was conjugated with Texas Red;
7. With labelled extension primer of duplex A as tracer, control;
8. With labelled extension primer of duplex A as tracer, sample;
9. With labelled lagging probe of duplex B as tracer, control;
10. With labelled lagging probe of duplex B as tracer, sample;
11. With labelled extension primer of duplex A and labelled lagging probe of duplex B probes as tracers, blank;
12. Same as lane 11, control;
13. Same as lane 11, sample;
14. With labelled lagging probe of duplex A as tracer, blank;
15. With labelled lagging probe of duplex A as tracer, control;
16. With labelled lagging probe of duplex pair A as tracer, sample.

In the presence or absence of the specific template, non-specific amplification was evident in PCR by smears of bands including large molecule weight by-products (lane 2, 3, 5 and 6). In contrast, polymerase dependent strand displacement eliminated nearly all non-specific amplification (lanes 8, 9, 12 and 13). Using either Stoffel fragment (FIG. 4a) or Taq DNA polymerase (FIG. 4b) yielded nearly identical results, except that exonuclease activity was absent when the Stoffel fragment was used (FIG. 4a, lane 16). This experiment demonstrates the dramatic contrast between standard PCR and the improved method of the invention with respect to specificity of amplification.

EXAMPLE 5

A Homogeneous Assay for Detection of HBV Sequence

A homogeneous assay based on polymerase dependent strand displacement is described herein. This example demonstrates the sensitivity of the homogeneous assay in the quantitative detection of a HBV sequence in human genomic DNA. Detection of amplification is based on the energy transfer of two different fluorophores which have been conjugated to oligonucleotide primers or probes.

The probe pairs are illustrated in FIG. 9. Referring to the figure, "L" indicates a carbon linker used to modify the 3' terminal hydroxy group of lagging probe Sequence I.D. Number 9 to prevent its use as a primer of an extension reaction. "$T_r$" and "F" indicate amino modified thymidine bases which have been conjugated with the fluorophores Texas Red and fluorescein in extension primer Sequence I.D. Number 10 and lagging probe Sequence I.D. Number 11, respectively.

Figure 5A:
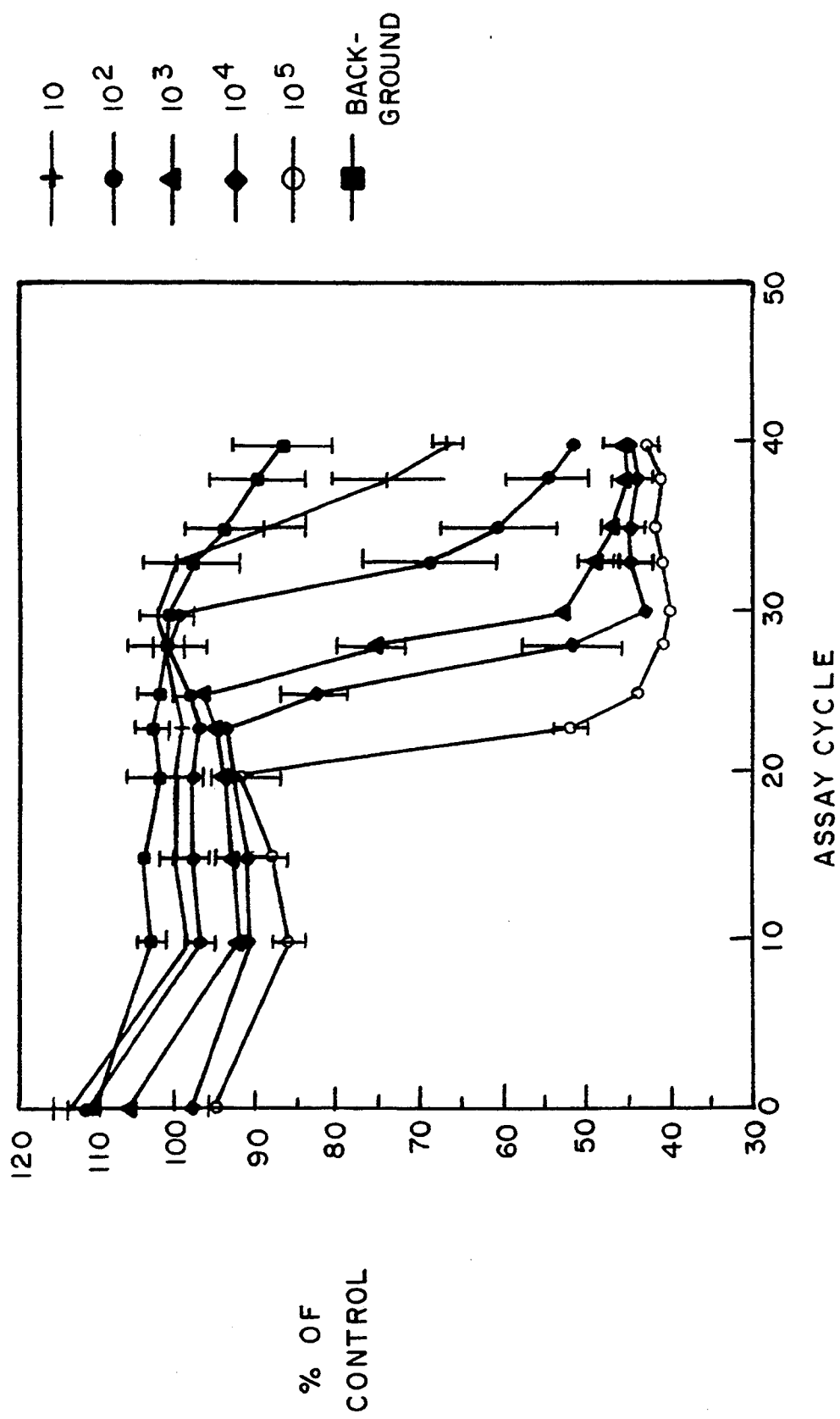
FIG. 5A and 5B show the results of the homogeneous assay of the invention for the detection of the HBV sequence.

In a reaction volume of 20 ul, 40 ng of each probe was added into a buffer containing 50 mM TrisHCl pH=8.3, 2 mM NH$_4$Cl, 40 mM KCl, 2 mM DTT, 10 mM MgCl$_2$, 125 uM dXTPs and 0.1% of triton X-100. Various amounts of HBV target sequence as indicated in FIG. 5A, and a plasmid containing the genomic sequence of an adr substrain of HBV virus were added. The amount of target sequence was estimated by the absorbance at 260 run. The reactions were performed in the wells of a 96-well microtiter plate. A fluorescence microtiter plate reader was used to measure the signal generated by the fluorophores. At various amplification cycles, the reporting signal was detected by measuring the relative fluorescence intensity at 630 nm, using an excitation wavelength at 495 nm. The operating profile for each amplification cycle consisted of: 94° C. for 0.5 min., 55° C. for 0.5 min. and 65° C. for 1 minute. The control sample contained no polymerase. The "Background" control contained 1 ug of Hela cell DNA instead of HBV plasmid.

Figure 5B:
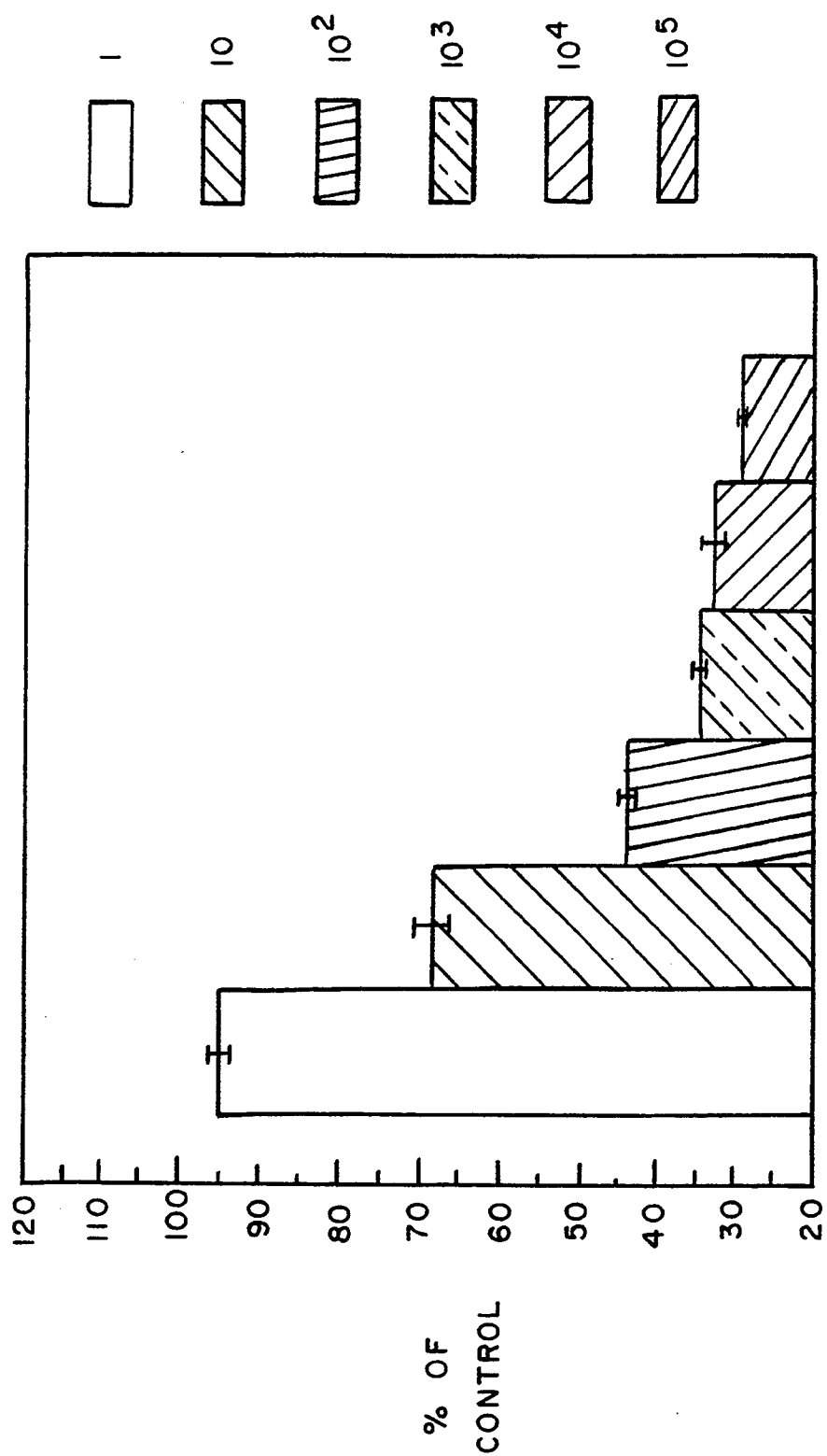

The results are shown in FIGS. 5A and 5B. FIG. 5A shows the detection of polymerase dependent strand-displacement for various amounts of target sequence as a function of amplification cycle number. The results demonstrate a positive correlation between the amount of target sequence initially present and the amount of amplified product. FIG. 5B shows the sensitivity of polymerase dependent strand-displacement for various amounts of target sequence at cycle 40. The limit of detection was estimated at about 10 molecules.

Figure 6:
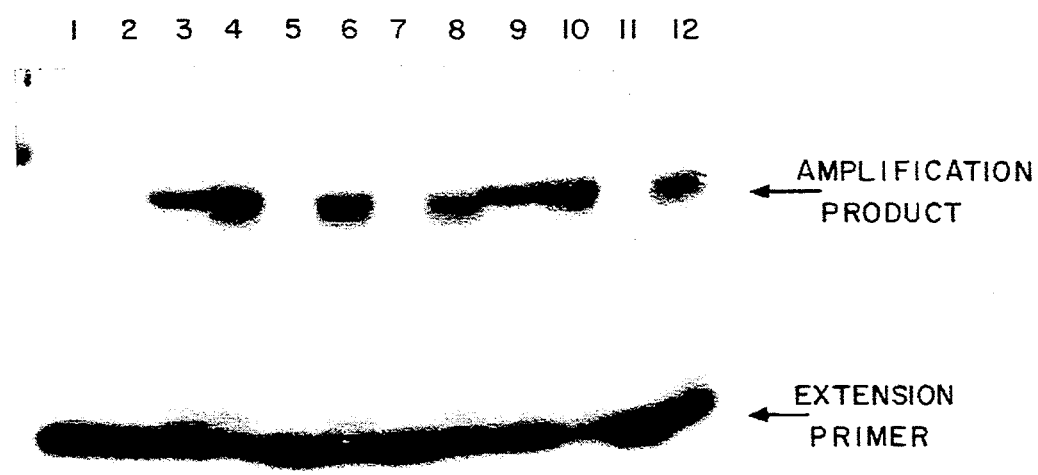
FIG. 6 shows an autoradiogram of PAGE gel illustrating the agreement between the visual observation of product by strand-displacement amplification and signal analysis of similar detection process presented in FIG. 5A and FIG. 5B.

The homogeneous assay is a rapid, sensitive and quantitative method for nucleic acid based diagnostic applications. The quantitative results obtained using the homogeneous assay correlate well with the results obtained using traditional polyacrylamide analysis (FIG. 6). FIG. 6 shows an autoradiograph of the amplification product corresponding to the HBV sequence. These results were obtained using a three-probe configuration: extension primer Sequence I.D. Number 12, extension primer Sequence I.D. number 13 and lagging probe Sequence I.D. Number 14. (FIG. 10). The reaction conditions were the same as those previously described, with the exception that the probes of FIG. 10 were substituted for those probes previously used and 5' end $^{32}$P labelled extension primer Sequence I.D. Number 12 was added as tracer. An aliquot was taken for polyacrylamide gel analysis following amplification cycles 25 and 35. The results are shown in FIG. 6. The identification of each lane is as follows:

Lane 1: Control, 25 cycles;
Lane 2: Control, 35 cycles;
Lane 3: HBV plasmid, $10^5$ molecules, 25 cycles;
Lane 4: HBV plasmid, $10^5$ molecules, 35 cycles;

Lane 5: HBV plasmid, $10^3$ molecules, 25 cycles;
Lane 6: HBV plasmid, $10^3$ molecules, 35 cycles;
Lane 7: HBV plasmid, 10 molecules, 25 cycles;
Lane 8: HBV plasmid, 10 molecules, 35 cycles;
Lane 9: Sample 1, DNA from patient serum, 25 cycles;
Lane 10: Sample 1, DNA from patient serum, 35 cycles;
Lane 11: Sample 2, DNA from patient serum, 25 cycles;
Lane 12: Sample 2, DNA from patient serum, 35 cycles.

The autoradiography results agreed well with the fluorometric measurements obtained using the homogeneous assay.

The foregoing description of the invention and the Examples demonstrating the application of the invention, are but exemplary of the various ways the invention can be utilized. The present invention has also been applied successfully to other target sequences e.g. a conserved sequence from the IE II region of human cytomegalovirus and the conserved coding sequence from the human sex-determining region. That other variations will be useful will be apparent to those skilled in the art. Therefore, the present invention is to be considered limited only by the appended claims.

We claim:

1. In a method for a polymerase dependent extension reaction for synthesizing an extension product complementary to a target nucleic acid within a larger nucleic acid template comprising:

combining a pair of primers with said nucleic acid template;

and performing said polymerase dependent extension reaction under conditions sufficient to synthesize said extension product, the improvement comprising:

combining said pair of primers with the nucleic acid template in the presence of at least one energy sink oligonucleotide that is incapable of acting as a primer in an extension reaction, wherein each of said at least one energy sink oligonucleotides has sufficient complementarity to at least one of said primers and is present in sufficient concentration so as to competitively inhibit binding of said primer to a non-target nucleic acid via hybridization of said energy sink oligonucleotide to said primer.

2. The method of claim 1, wherein the 3' end of at least one of said primers protrudes when hybridized to said energy sink oligonucleotide.

3. The method of claim 1, wherein the energy sink oligonucleotide has at least 10 consecutive bases perfectly complementary to a 10 base sequence in the one of the primers.

4. The method of claim 1, wherein a lagging probe having a reporting group attached thereto is hybridized to the nucleic acid template at a position downstream of the direction of elongation, the method further comprising:

utilizing elongation of the primer to displace the lagging probe from the template and measuring a change in a signal resulting from the displacement of the lagging probe from the nucleic acid template.

5. The method of claim 1, wherein a lagging probe is hybridized to the nucleic acid template at a position downstream of the direction of elongation, and wherein the primer and the lagging probe are labeled such that the generation of a signal depends upon the juxtaposition of the labelled primer and the labelled lagging probe, the method further comprising:

utilizing elongation of the primer to displace the lagging probe from the template and measuring a change in a signal resulting from the displacement of the lagging probe from the nucleic acid template.

6. A method for amplifying and detecting a target nucleic acid sequence in a nucleic acid template in the same vessel, the method comprising:

a) providing in the presence of the nucleic acid template, a first duplex and a second duplex, the first duplex including a first primer and a first energy sink oligonucleotide, the second duplex including a second primer and a second energy sink oligonucleotide, wherein the first energy sink oligonucleotide is of sufficient complementarity to the first primer so as to competitively inhibit binding of the first primer to a non-target sequence in the nucleic acid template and wherein the second energy sink oligonucleotide is of sufficient complementarity to the second primer so as to competitively inhibit binding of the second primer to the non-target sequence, wherein the first energy sink oligonucleotide and the second energy sink oligonucleotide are incapable of acting as extension primers in an extension reaction;

b) allowing the first primer, the first energy sink oligonucleotide, the second primer and the second energy sink oligonucleotide to hybridize to the template so that the first energy sink oligonucleotide hybridizes to the template at a position downstream of the direction of elongation of the second primer and the second energy sink oligonucleotide hybridizes to the template at a position downstream of the direction of elongation of the first primer, wherein at least one of the first energy sink oligonucleotide and the second energy sink oligonucleotide has a reporting group attached thereto;

c) subjecting the template having the primers and the energy sink oligonucleotides hybridized thereto to conditions sufficient to permit the first primer to elongate sufficiently to displace the second energy sink oligonucleotide and the second primer to elongate sufficiently to displace the first energy sink oligonucleotide from the template, and d) measuring a change in a signal resulting from the displacement of the energy sink oligonucleotide having the reporting group attached thereto from the template.

7. The method of claim 6, wherein the reporting group is selected from the group consisting of a fluorophore, a chromophore and a specific binding agent.

8. The method of claim 7, wherein the reporting group is a fluorophore.

9. The method of claim 6, wherein at least one of the primers has a reporting group attached thereto, wherein the primer having the reporting group attached thereto and the energy sink oligonucleotide having the reporting group attached thereto are labelled such that a first signal is measurable when the labeled primer and the labeled energy sink oligonucleotide are juxtaposed and a second signal is measurable when the labeled primer and the labeled energy sink oligonucleotide are not juxtaposed with one another.

10. The method of claim 9, wherein the reporting group attached to the primer and the reporting group attached to the energy sink oligonucleotide are fluorophores with overlapping emission and excitation wavelengths.

11. The method of claim 6, wherein at least one of the primers has a reporting group attached thereto, wherein the primer having the reporting group attached thereto and the energy sink oligonucleotide having the reporting group attached thereto are labelled such that juxtaposition of the labeled primer and the labeled energy sink oligonucleotide results in quenching of a signal emitted by the reporting group attached to the primer or by the reporting group attached to the energy sink oligonucleotide.

12. A kit for use in a polymerase dependent extension reaction that utilizes a pair of primers to synthesize an extension product complementary to a target sequence in a nucleic acid template wherein binding of at least one of the primers to a non-target sequence is prevented, the kit consisting essentially of:
a duplex containing a primer and an energy sink oligonucleotide that is incapable of acting as an extension primer in an extension reaction, wherein the energy sink oligonucleotide is sufficiently complementary to the primer to competitively inhibit binding of the primer to the non-target sequence.

13. The kit of claim 12, wherein the energy sink oligonucleotide has a 5' end, and wherein the 3' end of the extension primer protrudes beyond the 5' end of the energy sink oligonucleotide when the primer and the energy sink oligonucleotide are hybridized to one another.

14. A kit for use in a polymerase dependent extension reaction that utilizes a pair of primers to synthesize an extension product complementary to a target sequence in a nucleic acid template wherein binding of at least one of the primers to a non-target sequence is prevented, the kit consisting essentially of:
a first duplex containing a first primer and a first energy sink oligonucleotide that is incapable of acting as an extension primer in an extension reaction, wherein the first energy sink oligonucleotide is complementary to the first primer; and
a second duplex containing a second primer and a second energy sink oligonucleotide that is incapable of acting as an extension primer in an extension reaction, wherein the second energy sink oligonucleotide is complementary to the second primer;
wherein the first energy sink oligonucleotide and the second energy sink oligonucleotide competitively inhibit binding of the primers to the non-target sequence, and further, wherein the first primer and the second energy sink oligonucleotide each are labeled with a different reporting group such that a first signal is measurable when the first primer and second energy sink oligonucleotide are juxtaposed and wherein a second signal is measurable when the first primer and the second energy sink oligonucleotide are not juxtaposed with one another.

15. The method of claim 14, wherein juxtaposition of the labeled primer and the labeled energy sink oligonucleotide results in quenching of a signal emitted by the reporting group attached to the first primer or by the reporting group attached to the second energy sink oligonucleotide.

16. The kit of claim 14, wherein both of the energy sink oligonucleotides have a 5' end and wherein the 3' end of at least one of the primers protrudes beyond the 5' end of its complementary energy sink oligonucleotide when the primer and the energy sink oligonucleotide are hybridized to one another.

* * * * *

SEQUENCE LISTING ( 1 ) GENERAL INFORMATION:

( i i i ) NUMBER OF SEQUENCES: 14

( 2 ) INFORMATION FOR SEQ ID NO: 1:

( i ) SEQUENCE CHARACTERISTICS:
( A ) LENGTH: 16 nucleotides
( B ) TYPE: nucleic acid
( C ) STRANDEDNESS: single stranded
( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 1:

ACCCGGGGAT CCTCTA    16

( 2 ) INFORMATION FOR SEQ ID NO: 2:

( i ) SEQUENCE CHARACTERISTICS:
( A ) LENGTH: 14 nucleotides
( B ) TYPE: nucleic acid
( C ) STRANDEDNESS: single stranded
( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 2:

AGAGTCGACC TGCA    14

( 2 ) INFORMATION FOR SEQ ID NO: 3:

( i ) SEQUENCE CHARACTERISTICS:
( A ) LENGTH: 29 nucleotides
( B ) TYPE: nucleic acid
( C ) STRANDEDNESS: single stranded
( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 3:

TGGGCCCCTA GGAGATATCT CAGCTGGAC    29

( 2 ) INFORMATION FOR SEQ ID NO: 4:

( i ) SEQUENCE CHARACTERISTICS:
    ( A ) LENGTH: 18 nucleotides
    ( B ) TYPE: nucleic acid
    ( C ) STRANDEDNESS: single stranded
    ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 4:

TGTATTTGGA GGTCAGCT        18

( 2 ) INFORMATION FOR SEQ ID NO: 5:

( i ) SEQUENCE CHARACTERISTICS:
        ( A ) LENGTH: 20 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 5:

TTGCCATAAA CCTCCAGTCG        20

( 2 ) INFORMATION FOR SEQ ID NO: 6:

( i ) SEQUENCE CHARACTERISTICS:
        ( A ) LENGTH: 27 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 6:

GCACCGTGCT GACCTCCAAA TACCGTT        27

( 2 ) INFORMATION FOR SEQ ID NO: 7:

( i ) SEQUENCE CHARACTERISTICS:
        ( A ) LENGTH: 18 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 7:

TCGACTGGAG GTTTATGT        18

( 2 ) INFORMATION FOR SEQ ID NO: 8:

( i ) SEQUENCE CHARACTERISTICS:
        ( A ) LENGTH: 38 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 8:

TCCTAGGACC CCCTGCTCGT GTTACAGGCG GGGTTTTT    38

( 2 ) INFORMATION FOR SEQ ID NO: 9:

( i ) SEQUENCE CHARACTERISTICS:
        ( A ) LENGTH: 17 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 9:

AATGTCCGCC CCAAAAA    17

( 2 ) INFORMATION FOR SEQ ID NO: 10:

( i ) SEQUENCE CHARACTERISTICS:
        ( A ) LENGTH: 27 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 10:

GGTATTGTGA GGATTCTTGT CAACAAG    27

( 2 ) INFORMATION FOR SEQ ID NO: 11:

( i ) SEQUENCE CHARACTERISTICS:
        ( A ) LENGTH: 25 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 11:

AAATAACACT CCTAAGAACA GTTGT    25

( 2 ) INFORMATION FOR SEQ ID NO: 12:

( i ) SEQUENCE CHARACTERISTICS:
        ( A ) LENGTH: 21 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 12:

TGGCTCAGTT TACTAGTGCC A            2 1

( 2 ) INFORMATION FOR SEQ ID NO: 13:

( i ) SEQUENCE CHARACTERISTICS:
        ( A ) LENGTH: 27 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 13:

GGAAAGCCCT ACGAACCACT GAACAAA            2 7

( 2 ) INFORMATION FOR SEQ ID NO: 14:

( i ) SEQUENCE CHARACTERISTICS:
        ( A ) LENGTH: 23 nucleotides
        ( B ) TYPE: nucleic acid
        ( C ) STRANDEDNESS: single stranded
        ( D ) TOPOLOGY: linear ( i i ) MOLECULE TYPE: other nucleic acid ( i i i ) HYPOTHETICAL: no ( i v ) ANTI-SENSE: no ( x i ) SEQUENCE DESCRIPTION: SEQ ID NO: 14:

AATCGGGATG CTTGGTGACT TGT            2 3